US010905775B2

(12) United States Patent
Mayer et al.

(10) Patent No.: US 10,905,775 B2
(45) Date of Patent: *Feb. 2, 2021

(54) PARTICULATE CONSTRUCTS FOR RELEASE OF ACTIVE AGENTS

(71) Applicants: CELATOR PHARMACEUTICALS, INC., Palo Alto, CA (US); The Trustees of Princeton University, Princeton, NJ (US)

(72) Inventors: Lawrence D. Mayer, North Vancouver (CA); Robert K. Prud'homme, Lawrenceville, NJ (US); Christine J. Allen, Toronto (CA); Walid S. Saad, Princeton, NJ (US)

(73) Assignees: Celator Pharmaceuticals, Inc., Palo Alto, CA (US); The Trustees of Princeton University, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/905,015

(22) Filed: May 29, 2013

(65) Prior Publication Data
US 2013/0336915 A1 Dec. 19, 2013

Related U.S. Application Data

(63) Continuation of application No. 11/632,884, filed as application No. PCT/US2005/025549 on Jul. 19, 2005, now abandoned.

(60) Provisional application No. 60/589,164, filed on Jul. 19, 2004.

(51) Int. Cl.
A61K 47/54 (2017.01)
A61K 47/69 (2017.01)
A61K 47/59 (2017.01)
A61K 47/60 (2017.01)
B82Y 5/00 (2011.01)
A61K 8/85 (2006.01)
A61K 9/51 (2006.01)
A61K 45/06 (2006.01)
A61Q 17/04 (2006.01)
A61K 47/55 (2017.01)
A61K 47/58 (2017.01)
A61K 47/22 (2006.01)

(52) U.S. Cl.
CPC ............ A61K 47/6931 (2017.08); A61K 8/85 (2013.01); A61K 9/5153 (2013.01); A61K 45/06 (2013.01); A61K 47/22 (2013.01); A61K 47/54 (2017.08); A61K 47/543 (2017.08); A61K 47/545 (2017.08); A61K 47/55 (2017.08); A61K 47/551 (2017.08); A61K 47/552 (2017.08); A61K 47/58 (2017.08); A61K 47/59 (2017.08); A61K 47/593 (2017.08); A61K 47/60 (2017.08); A61K 47/6935 (2017.08); A61Q 17/04 (2013.01); B82Y 5/00 (2013.01); A61K 2800/57 (2013.01)

(58) Field of Classification Search
None
See application file for complete search history.

(56) References Cited

U.S. PATENT DOCUMENTS

| | | |
|---|---|---|
| 4,610,868 A | 9/1986 | Fountain et al. |
| 4,780,535 A | 10/1988 | Theodoropulos |
| 5,145,684 A | 9/1992 | Liversidge et al. |
| 5,166,319 A | 11/1992 | Wrasidlo |
| 5,188,837 A | 2/1993 | Domb |
| 5,330,768 A | 7/1994 | Park et al. |
| 5,336,506 A | 8/1994 | Josephson et al. |
| 5,470,583 A | 11/1995 | Na et al. |
| 5,543,158 A | 8/1996 | Gref et al. |
| 5,766,818 A | 6/1998 | Smith et al. |
| 5,869,103 A | 2/1999 | Yeh et al. |
| 5,891,475 A | 4/1999 | Perrin et al. |
| 5,928,832 A | 7/1999 | Smith et al. |
| 6,429,200 B1 | 8/2002 | Monahan et al. |
| 6,482,413 B1 | 11/2002 | Chalasani et al. |
| 6,500,461 B2 | 12/2002 | Perkins et al. |
| 6,559,243 B1 | 5/2003 | Heinzman et al. |
| 6,589,548 B1 * | 7/2003 | Oh et al. ............. 424/426 |
| 6,673,612 B2 | 1/2004 | Monahan et al. |
| 6,676,963 B1 | 1/2004 | Lanza et al. |
| 2004/0152913 A1 | 8/2004 | Caprioli et al. |
| 2004/0221989 A1 | 11/2004 | Zhou et al. |
| 2004/0247680 A1 * | 12/2004 | Farokhzad et al. ......... 424/486 |

FOREIGN PATENT DOCUMENTS

| | | | |
|---|---|---|---|
| JP | 63-139972 | 6/1988 | |
| JP | 2003-026604 | 1/2003 | |
| WO | WO-95/31217 | 11/1995 | |
| WO | WO-01/52826 | 7/2001 | |
| WO | WO-02/076970 | 10/2002 | |
| WO | WO 02078674 A1 * | 10/2002 | ............. A01N 25/04 |

(Continued)

OTHER PUBLICATIONS

Soppimath et al. Journal of Controlled Release, 70, p. 1-20, 2001.*
Muggia et al. J CLin Oncol 18(1), p. 106-115, 2000.*
McLeod et al. International Journal of Pharmaceutics, 92, p. 105-114, 1993.*
Definition of "coordinate" from Merriam-Webster online, accessed May 12, 2014.*
PubMed abstract for Sun et al. Zhonghua Nan Ke Xue, 10(9), p. 658-61, 666, Sep. 2004.*

(Continued)

Primary Examiner — Nissa M Westerberg
(74) Attorney, Agent, or Firm — Morrison & Foerster LLP

(57) ABSTRACT

Particulate constructs stabilized by amphiphilic copolymers and comprising at least one active coupled to a hydrophobic moiety provide sustained release of the active in both in vitro and in vivo environments.

8 Claims, 3 Drawing Sheets

(56) References Cited

FOREIGN PATENT DOCUMENTS

| WO | WO-02/098465 | 12/2002 |
|---|---|---|
| WO | WO-03/028696 | 4/2003 |
| WO | WO-04/087105 | 10/2004 |
| WO | WO-04/087115 | 10/2004 |

OTHER PUBLICATIONS

Murad et al. Oncology "Gemcitabine and Paclitaxel as Salvage Therapy in Metastatic Breast Cancer", Feb. 2001.*
Spectrum Cemical page for Poloxamer-407, (https://www.spectrumchemical.com/OA_HTML/index.jsp?section=10565&language=US&minisite=10020&respid=22372), accessed Oct. 20, 2016.*
Gonzalez-Lopez, Jaime, et al. "Self-associative behavior and drug-solubilizing ability of poloxamine (tetronic) block copolymers." Langmuir 24.19 (2008): 10688-10697.*
Office Action for EP 05 773 414.7, dated Mar. 14, 2013.
Vodovozova et al., "Antitumour activity of cytotoxic liposomes equipped with selection ligand SiaLex, in a mouse mammary adenocarcinoma model", European Journal of Cancer (2000) 36:942-949.
Olbrich et al., "Lipid-Drug-Conjugate (LDC) Nanoparticles as Novel Carrier System for the Hydrophilic Antitrypanosomal Drug Diminazenediaceturate," Journal of Drug Targeting (2002) 10(5):387-396.
Shiah et al., "Combination chemotherapy and photodynamic therapy of targetable N-(2-hydroxypropyl)methacrylamide copolymer-doxorubicin/mesochlorin e6-OV-TL 16 antibody immunoconjugates," Journal of Controlled Release (2001) 74:249-253.
Supplementary European Search Report for EP 05773414.7, dated Sep. 29, 2010, 11 pages.
Torchilin et al., "Liposomes and Micelles to Target the Blood Pool for Imaging Purposes," Journal of Liposome Research (2000) 10(4):483-499.
Trubetskoy et al., "Use of polyoxyethylene-lipid conjugates as long-circulating carriers for delivery of therapeutic and diagnostic agents," Advanced Drug Delivery Reviews (1995) 16(2-3):311-320.
Alkan-Onyuksel et al., Pharm. Res. (1994) 11:206-212.
Fonseca et al., Journal of Controlled Release (2002) 83:273-286.
Frerot et al., Eur. J. Org. Chem. (2003) 967-971.
Greenwald et al., Critical Reviews in Therapeutic Drug Carrier Systems (2000) 17:101-161.
Greenwald et al., Journal of Controlled Release (2001) 74:159-171.
Greenwald et al., Journal of Medicinal Chemistry (1996) 39:424-431.
Gref et al., Colloids Surf B Biointerfaces (2000) 18:301-313.
International Search Report for PCT/US05/025549, dated Aug. 14 2006, 1 page.
Kim et al. J. Cont. Rei. (2000) 65:345-358.
Lamprecht et al., Int. J. Pharmaceut. (2000) 196:177-182.
Lemoine et al., Biomaterials (1996) 17:2191-2197.
Lundberg, J. Pharm. Pharmacal. (1997) 49:16-21.
Mu et al., Journal of Controlled Release (2003) 86:33-48.
Nishiyama et al., J. Cancer Res. (2003) 63:8977-8983.
Nishiyama et al., Journal of Controlled Release (2001) 74:83-94.
Notice of the grounds for rejection (translation) for JP 2007-522647, dated Sep. 6, 2011, 3 pages.
Ohya et al. Polym Adv Technol (2000) 11:635-641.
Perkins et al. Int. J. Pharmaceut. (2000) 200:27-39.
Trubetskoy et al., "Use of polyoxyethylene-lipid conjugates as long-circulating carriers for delivery of therapeutic and diagnostic agents," Advanced Drug Delivery Reviews (1995) 16(2-3):311-320 (abstract only).
Wheeler et al., Pharm. Sciences (1994) 83:1558-1564.
Li, "Poly(L-glutamic acid)—anticancer drug conjugates," Adv Drug Deliv Rev (2002) 54(5):695-713.
Tracy et al., "Factors affecting the degradation rate of poly(lactide-co-glycolide) microspheres in vivo and in vitro," Biomaterials (1999) 20(11):1057-1062.
Hayashi et al., "The effects of delayed treatment with sialyl Lewis X against lipopolysaccharide-induced acute lung injury in rabbits," European Journal of Pharmacology (2000) 392:109-116.
Soo et al., "Incorporation and Release of Hydrophobic Probes in Biocompatible Polycaprolactone-block-poly(ethylene oxide) Micelles: Implications for Drug Delivery," Langmuir (2002) 18:9996-10004.
Summons to attend oral proceedings pursuant to Rule 115(1) EPC for EP 05773414.7, issued Oct. 6, 2016, 10 pages.

* cited by examiner

2A

2B

Delivery Vehicle Formulations of Drug Combinations Containing Hydrophobic Polymer-Based Drug Conjugates

Step 1: Prepare block co-polymer and conjugate drugs individually onto hydrophobic polymer via a chemical linker

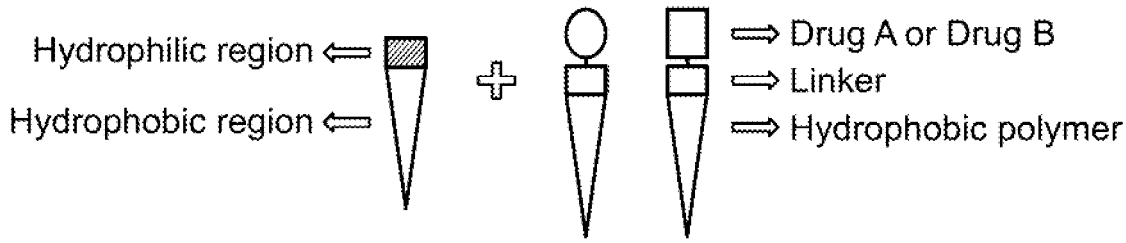

Step 2: Mix desired ratios of Drug A and Drug B hydrophobic polymer conjugate in combination with block co-polymer to form stable drug delivery particles.

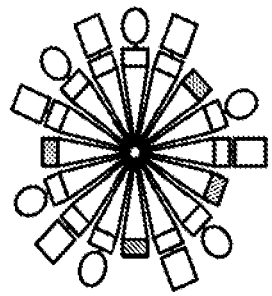

Step 3: After administration *in vivo*, drug release rates are dictated by kinetics of linker degradation.

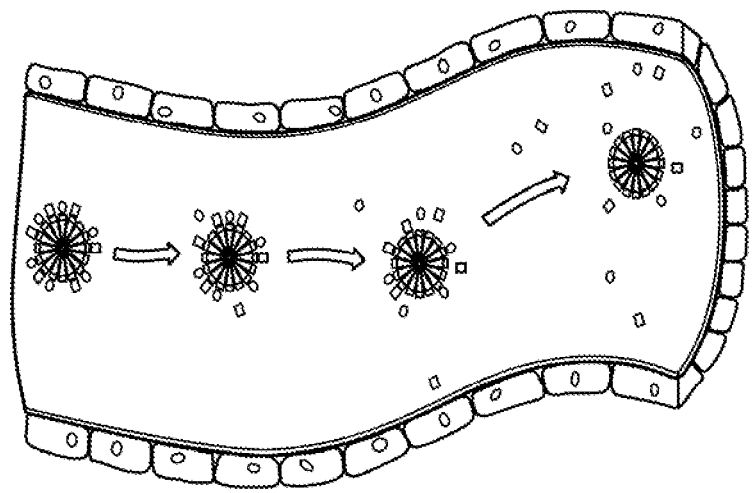

*FIG. 3*

PARTICULATE CONSTRUCTS FOR RELEASE OF ACTIVE AGENTS

RELATED APPLICATIONS

This application is a continuation of U.S. patent application Ser. No. 11/632,884, having an international filing date of 19 Jul. 2005, which is the national phase of PCT application PCT/US2005/025549 having an international filing date of 19 Jul. 2005, which claims benefit under 35 U.S.C. §119(e) to provisional application 60/589,164 filed 19 Jul. 2004. The contents of these documents are incorporated herein by reference in their entirety.

TECHNICAL FIELD

The description relates to compositions and methods for improved delivery and performance of active agents. More particularly, the invention concerns particulate constructs stabilized by an amphiphilic compound and comprising at least one active agent coupled through a linker to a hydrophobic moiety, which agent can be released from the construct by cleavage of the linker.

BACKGROUND ART

Sustained release is desirable in many applications to provide optimal use and effectiveness of active agents, including pharmaceuticals, cosmetics, food, and fragrances. Attempts have been made to solubilize, target, stabilize, and control the release of substances, including use of microparticles, nanoparticles, and polymer conjugation.

Approaches based on using polymer encapsulation to formulate substances in microparticles or larger matrices have succeeded in delaying their release. In such formulations, the release of the encapsulated subsequence is controlled by diffusion out of the polymer or by erosion of the matrix itself. This approach is not effective in smaller particles, such as nanoparticles. Nanoparticulate dimensions may be required in a number of applications, such as drug delivery, in particular to tumors where particulates in the size range <200 nm accumulate in tumors whereas larger particles do not. While the art provides many descriptions for preparation of nanoparticles containing active agents, none is completely satisfactory. See, e.g., Mu, L., et al., *Journal of Controlled Release* (2003) 86:33-48; Fonseca, C., et al., *Journal of Controlled Release* (2002) 83:273-286.

Another strategy used to achieve controlled release has been through the use of polymer conjugates of actives with cleavable groups. (Frerot, E., et al., *European Journal of Organic Chemistry* (2003) 967-971.) A common polymer used in drug delivery is poly(ethylene glycol) (PEG) (Greenwald, R. B., et al., *Critical Reviews in Therapeutic Drug Carrier Systems* (2000) 17:101-161; Greenwald, R. B., *Journal of Controlled Release* (2001) 74:159-171). Conjugation of drugs to PEG has been shown to provide long circulation times in vivo, and increases the solubility of hydrophobic drug. Pharmaceutically active proteins have also been coupled to PEG, resulting in alteration of properties; increased bioavailability, decreased immunogenicity, and enhanced solubility. While this strategy provided sustained in vitro drug release profiles, the drug release profiles in vivo showed significantly faster rates. (Greenwald, R. B., et al., *Journal of Medicinal Chemistry* (1996) 39:424-431.)

The literature with respect to controlled release systems and particulate carriers for pharmaceuticals and other compounds is extensive, and the following represent only illustrative documents.

U.S. Pat. Nos. 6,429,200 and 6,673,612 describe reverse micelles for carrying nucleic acids or other actives into cells. U.S. Pat. No. 6,676,963 describes nanoparticulate formulations for targeted drug delivery to tissues and organs. PCT publication WO 02/098465 describes lipid-based vehicles for delivery of pharmaceuticals comprising an internalizing peptide. PCT publication WO 03/028696 describes particulate delivery vehicles for coordinating the release of combinations of drugs. A multiplicity of liposomal formulations have been used for many years to deliver drugs.

Chelators for release of platinum-containing antitumor agents are described, for example, by Nishiyama, N., et al., *J. Controlled Release* (2001) 74:83-94 and by Nishiyama, N., et al., *J. Cancer Res.* (2003) 63:8977-8983.

Drug preparations have been formulated using mixed micellar and emulsion type formulations, including the use of PEG-modified phospholipids to stabilize oil in water emulsions. (Alkan-Onyuksel, et al., *Pharm. Res.* (1994) 11:206-212; Lundberg, *J. Pharm. Pharmacol.* (1997) 49:16-21; Wheeler, et al., *Pharm. Sciences* (1994) 83:1558-1564).

For example, U.S. Pat. No. 4,610,868 describes a matrix material having a particle size in the range of 500 nm-100 µm which is composed of a hydrophobic compound and an amphipathic compound. The resulting "lipid matrix carriers" encapsulate biologically active agents and effect release from the matrix. U.S. Pat. No. 5,869,103 describes particulate compositions in the size range of 10 nm-200 µm where the particles are formed by combining emulsions of an active agent with mixtures of a biodegradable polymer and a water-soluble polymer.

U.S. Pat. No. 5,145,684 describes particulate preparations wherein a crystalline drug substance is itself coated with a surface modifier. Similarly, U.S. Pat. No. 5,470,583 describes nanoparticles having nonionic surfactants as a surface modifier associated with a charged phospholipid. The biologically active substance, itself having a particle size of <400 nm, is used as the core of the particles.

U.S. Pat. No. 5,891,475 describes drug delivery vehicles which contain hydrophilic cores such as those prepared from polysaccharides. The particles are treated to contain an external layer of fatty acids grafted onto the core by covalent bonds.

U.S. Pat. No. 5,188,837 describes microparticles which are generally in the size range of 1-38 µm which contain a solid hydrophobic polymer as a core and a phospholipid, such as phosphatidyl choline or lecithin as an exterior coating. According to this disclosure, other phospholipids such as phosphatidyl inositol and phosphatidyl glycerol are unworkable in this system. U.S. Pat. No. 5,543,158 discloses 1 nm-1 µm particles with polymeric cores and a surface layer of PEG, which may be linked covalently to a biologically active agent contained therein.

Perkins, W. R., et al., *Int. J. Pharmaceut.* (2000) 200:27-39 describe "lipocores" which are formed from a core of a poorly water-soluble drug surrounded by a PEG-conjugated lipid.

Gref, R., et al., *Coll and Surf B: Biointerfaces* (2000) 18:301-313 describe the nature of protein absorption onto PEG-coated nanoparticles formed from various polymers and copolymers, including polycaprolactone. Although it is recognized that such particles might be useful in pharmaceutical applications, only the particles themselves were studied. Lemoine, D., et al., *Biomaterials* (1996) 17:2191-2197 reports studies of various nanoparticles composed of, among other polymers, polycaprolactone. While recognizing these as useful in delivery systems, only the particles themselves were studied.

Lamprecht, A., et al., *Int. J. Pharmaceut.* (2000) 196:177-182 reports the study of the effect of the use of microfluidizers on the particle size of nanoparticles obtained using various hydrophobic polymers and copolymers.

Kim, S-Y., et al., *J. Cont. Rel.* (2000) 65:345-358 describe copolymeric nanospheres of PLURONIC® (block copolymers of ethylene oxide and propylene oxide) with polycaprolactone (PCL). Nanospheres of PLURONIC®/PCL block copolymers having an average diameter of <200 nm were loaded with endomethicin and evaluated with regard to cytotoxicity, drug release, drug loading efficiency and physical characteristics. The particles are formed entirely of the block copolymer.

The literature regarding liposomal preparations for delivery and release of drugs is extensive; suffice it to say that the concept of encapsulating pharmaceuticals in liposomes is well established and highly nuanced.

Particulate constructs for sustained or controlled delivery of active agents is not confined to pharmaceuticals. For example, U.S. Pat. No. 5,928,832 describes latex emulsions containing toner for use in photocopying processes. U.S. Pat. No. 5,766,818 describes latex emulsions containing toner with hydrolyzable surfactants. U.S. patent publication 2004/0221989 describes surfactant compositions designed to decompose so as to reduce viscosity of their surroundings. U.S. 2004/0152913 describes cleavable surfactants for use in MALDI-MS analysis of hydrophobic proteins. U.S. Pat. No. 6,559,243 describes glyoxylic compounds coupled to active ingredients which are released on contact with an aqueous medium.

Despite the substantial number of preparations of microparticle, matrix chelator and nanoparticle formulations designed for drug delivery and other applications, an ideal composition has not been achieved.

One important application of controlled release delivery systems relates to the administration of drug combinations where it is desirable to coordinate the release of such drugs.

The progression of many life-threatening diseases such as cancer, AIDS, infectious diseases, immune disorders and cardiovascular disorders are influenced by multiple molecular mechanisms. Due to this complexity, achieving cures with a single agent has been met with limited success. Thus, combinations of agents have often been used to combat disease, particularly in the treatment of cancers. It appears that there is a strong correlation between the number of agents administered and cure rates for cancers such as acute lymphocytic leukemia and metastatic colorectal cancer. To date, virtually all curative regimens for cancer rely on drug combination cocktails in which optimal dosing schedules of agents with differing toxicities were determined in extensive post-marketing clinical trials.

Administration of free drug cocktails often results in rapid clearance of one or all of the drugs before reaching the tumor site. For this reason, many drugs have been incorporated into delivery vehicles designed to 'shield' them from mechanisms that would otherwise result in their clearance from the bloodstream. More relevant to the present invention, compositions wherein agents are encapsulated or otherwise associated with particulate delivery vehicles so that the vehicles control the pharmacokinetics and assure coordinated delivery are described in PCT application PCT/CA02/01500 as well as in PCT applications PCT/CA2004/000507 and PCT/CA2004/000508. The formulations of the present invention offer an alternative controlled release mechanism for these drug combinations.

DISCLOSURE OF THE INVENTION

The present invention provides particulate constructs that can be adapted to the release of active agents of various types useful in both pharmaceutical and non-pharmaceutical applications. These delivery systems provide high loading capacity for active compounds as well as provide a means for controlled release of the active, reduction in toxicity where relevant, and, if desired, selective delivery to a target site. The active agents may include various therapeutic agents such as platinum agents, taxanes and antibiotics, actives important in other applications such as pigments, dyes, fragrances and flavors, and may be applied in in vivo therapeutic and diagnostic contexts, in agricultural applications and in industrial uses.

Thus, in one aspect, the invention is directed to a particulate construct comprising an amphiphilic stabilizer, and a conjugate of the formula

(active-linker)$_n$-hydrophobic moiety    (1)

wherein n is an integer of 1-100; and wherein "active" refers to a compound that has a desired activity;

"linker" is a covalent bond, a divalent residue of an organic molecule or a chelator; and "hydrophobic moiety" refers to the residue of an organic molecule that is insoluble in aqueous solution.

In various embodiments, the active may be a fragrance, a pharmaceutical, a diagnostic agent, a toner, or any compound with a desirable activity. As noted in formula (1), a multiplicity of active compounds may be coupled to the same hydrophobic moiety, which may be a hydrophobic polymer with multiple linking sites, or a smaller molecule, such as a vitamin or steroid. More than one type of active agent may also be included, making the constructs particularly useful for combination therapy. In any event, by providing the delivery vehicle in this form, controlled release of the active, either over time or at a desired site, is facilitated.

Thus, in another aspect, the invention provides a method to deliver active compounds in a controlled manner over time or at a selected target.

BRIEF DESCRIPTION OF THE DRAWINGS

FIG. 3 provides a depiction of an exemplary delivery vehicle of the present disclosure including a combination of active agents/drugs. Three steps are depicted, including (1) preparation of the polymers, (2) mixture of the polymers and (3) administration of the delivery vehicle.

MODES OF CARRYING OUT THE INVENTION

Figure 1:
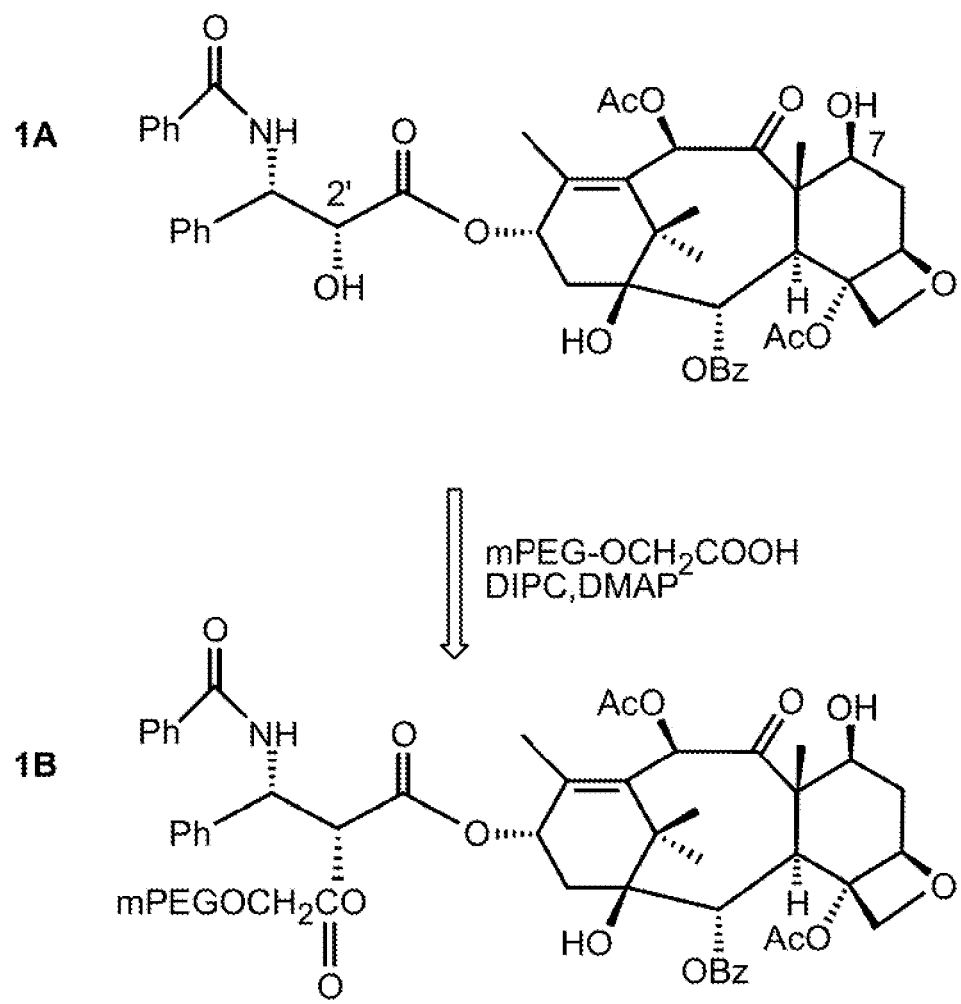
FIGS. 1A and 1B provide a depiction of poly(ethylene glycol) based paclitaxel prodrug prepared by the method of Greenwald, et al., *J. Med. Chem.* (1996) 39:424-431.

The present invention provides particularly advantageous particulate constructs which are adaptable to the controlled release of a wide variety of active agents. A single active agent may be released from a single particulate construct, or a multiplicity of such agents may be released. This may result from a multiplicity of such actives linked in a single conjugate to a hydrophobic moiety which can support covalent or chelator based linkage to a multiplicity of agents, and/or a multiplicity of such conjugates may be accommodated within a single particulate construct.

In describing the invention, the following meanings are attributed to the terms employed.

Unless defined otherwise, all terms of art, notations and other scientific terms or terminology used herein have the same meaning as is commonly understood by one of ordinary skill in the art to which this invention belongs. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

As used herein, "a" or "an" means "at least one" or "one or more."

The term "active agent" or "active" as used herein refers to chemical moieties used in a variety of applications including therapy or diagnosis. Examples are therapeutic agents, imaging agents, diagnostic agents, radionuclides, metal ions, inks, fragrances, viscoelastic agents, flavors, and, indeed, any chemical substance that has a desired behavior or activity. The solubility range of the actives ranges from "insoluble" in water or buffer, to those that are "sparingly soluble" or "soluble."

As used herein, "insoluble in aqueous medium" means that the substance can be dissolved in an aqueous solution at physiological ionic strength only to the extent of 0.05 mg/ml or less. It is recognized that almost no substances are completely insoluble in aqueous medium, and that the salt concentration or osmolality of the medium may also influence solubility. "Insoluble in aqueous medium," according to the present definition, assumes the osmolality, ionic strength, and pH of physiologically compatible solutions. Alternatively, "insolubility in pure water" may be used as the standard if so specified. "Insolubility in water" is defined as <0.05 mg/ml of pure water.

Similarly, "sparingly soluble" and "soluble" may be described in terms of reference to either "aqueous medium" as defined above or in "pure water." Substances that are "soluble" in aqueous medium dissolve at least to the extent of being equal to or greater than 1.0 mg/ml of the physiological solution; substances that are "sparingly soluble" in aqueous medium dissolve only to the extent of less than 1.0 mg/ml but more than 0.05 mg/ml of the physiological solution.

"Hydrophobic moiety" is defined as a moiety which is insoluble in aqueous solution as defined above. The hydrophobic moiety may be a hydrophobic polymer such as polycaprolactone or may be a hydrophobic small molecule such as a vitamin or a steroid. It may be monovalent—i.e., have a suitable functional group for coupling only to a single active through a linker—or may be multivalent—i.e., able to couple to multiple actives through a linker. Not all of the actives need be the same.

An "amphiphilic stabilizer" is a compound having a molecular weight greater than about 500 that has a hydrophilic region and a hydrophobic region. Preferably the molecular weight is greater than about 1,000, or greater than about 1,500, or greater than about 2,000. Higher molecular weight moieties, e.g., 25,000 g/mole or 50,000 g/mole, may be used. "Hydrophobic" is defined as above. "Hydrophilic" in the context of the present invention refers to moieties that have a solubility in aqueous solution (i.e., a physiological solution as defined above) of at least 1.0 mg/ml. Typical amphiphilic stabilizers are copolymers of hydrophilic regions and hydrophobic regions. Thus, in the amphiphilic stabilizer, the hydrophobic region, if taken alone, would exhibit a solubility in aqueous medium of less than 0.05 mg/ml and the hydrophilic region, if taken alone, would exhibit a solubility in aqueous medium of more than 1 mg/ml. Examples include copolymers of polyethylene glycol and polycaprolactone.

A "linker" refers to any covalent bond, to a divalent residue of a molecule, or to a chelator (in the case where the active is a metal ion or organic metallic compound, e.g., cisplatin) that allows the hydrophobic moiety to be attached to the active agent. The linker may be selectively cleavable upon exposure to a predefined stimulus, thus releasing the active agent from the hydrophobic moiety. The site of cleavage, in the case of the divalent residue of a molecule may be at a site within the residue, or may occur at either of the bonds that couple the divalent residue to the agent or to the hydrophobic moiety. The predefined stimuli include, for example, pH changes, enzymatic degradation, chemical modification or light exposure. Convenient conjugates are often based on hydrolyzable or enzymatically cleavable bonds such as esters, carbonates, carbamates, disulfides and hydrazones.

In some instances, the conditions under which the active performs its function are not such that the linker is cleaved, but the active is able to perform this function while still attached to the particle. In this case, the linker is described as "non-cleavable," although virtually any linker could be cleaved under some conditions; therefore, "non-cleavable" refers to those linkers that do not necessarily need to release the active from the particle as the active performs its function.

Exemplary Components

As noted previously, the members of the particulate constructs of the invention include: (1) an active agent; (2) a linker; (3) a hydrophobic moiety; and (4) an amphiphilic stabilizer. Examples of each of these follow:

Active Agents

In one application of the constructs of the invention, the constructs are used to deliver non-pharmaceutical or non-diagnostic agents including but not limited to pigments, inks, pesticides, herbicides, probes (including fluorescent probes), ingredients for sunscreens, fragrances and flavor compounds.

In another application of the constructs of the invention, the constructs are used to deliver pharmaceuticals or diagnostics in vivo. In these cases, the active is a therapeutic agent or a diagnostic agent.

A wide variety of therapeutic agents can be included. These may be anti-neoplastic agents, anthelmintics agents, antibiotics, anticoagulants, antidepressants, antidiabetic agents, antiepileptics, antihistamines, antihypertensive agents, antimuscarinic agents, antimycobacterial agents, immunosuppressants, antithyroid agents, antiviral agents, anxiolytic sedatives, astringents, beta-adrenoceptor blocking agents, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, biphosphonates, protease inhibitors, prostaglandins, radio-pharmaceuticals, sex hormones, steroids, anti-allergic agents, stimulants, sympathomimetics, thyroid agents, vasodilators and xanthines, disulfide compounds, antibacterials, antivirals, nonsteroidal anti-inflammatory drugs, analgesics, anticoagulants, anticonvulsants, antiemetics, antifungals, antihypertensives, anti-inflammatory agents, antiprotozoals, antipsychotics, cardioprotective agents, cytoprotective agents, antiarrhythmics, hormones, immunostimulating agents, lipid-lowering agents, platelet aggregation inhibitors, agents for treating prostatic hyperplasia, agents for treatment of rheumatic disease, or vascular agents (*Compendium of Pharmaceuticals and Specialties* (35$^{th}$ Ed.) incorporated herein by reference).

"Anti-neoplastic agent" refers to moieties having an effect on the growth, proliferation, invasiveness or survival of neoplastic cells or tumors. Anti-neoplastic therapeutic agents often include disulfide compounds, alkylating agents, antimetabolites, cytotoxic antibiotics, drug resistance modulators and various plant alkaloids and their derivatives. Other anti-neoplastic agents are contemplated.

Anti-neoplastic agents include paclitaxel, an etoposide-compound, a camptothecin-compound, idarubicin, carboplatin, oxaliplatin, adriamycin, mitomycin, ansamitocin, bleomycin, cytosine arabinoside, arabinosyl adenine, mercaptopolylysine, vincristine, busulfan, chlorambucil, melphalan, mercaptopurine, mitotane, procarbazine hydrochloride, dactinomycin, mitomycin, plicamycin, aminoglutethimide, estramustine phosphate sodium, flutamide, leuprolide acetate, megestrol acetate, tamoxifen citrate, testolactone, trilostane, amsacrine, asparaginase, interferon, teniposide, vinblastine sulfate, vincristine sulfate, bleomycin, methotrexate, valrubicin, carzelesin, paclitaxel, taxotane, camptothecin, doxorubicin, daunomycin, cisplatin, 5-fluorouracil, methotrexate; anti-inflammatory agents such as indomethacin, ibuprofen, ketoprofen, flubiprofen, dichlofenac, piroxicam, tenoxicam, naproxen, aspirin, and acetaminophen; sex hormones such as testosterone, estrogen, progestone, estradiol; antihypertensive agents such as captopril, ramipril, terazosin, minoxidil, and parazosin; anti-emetics such as ondansetron and granisetron; antibiotics such as metronidazole, and fusidic acid; cyclosporine; prostaglandins; biphenyl dimethyl dicarboxylic acid, carboplatin; antifungal agents such as itraconazole, ketoconazole, and amphotericin; steroids such as triamcinolone acetonide, hydrocortisone, dexamethasone, prednisolone, and betamethasone; cyclosporine, and functionally equivalent analogues, derivatives or combinations thereof.

Diagnostic agents may also be included as actives. These may comprise, for example, chelated metal ions for MRI imaging, radionuclides, such as $^{99}$Tc or $^{111}$In or other biocompatible radionuclides. These may also be therapeutic agents.

Linkers

The linker component, as described above, may be or may include a cleavable bond.

The linker may be, for example, cleaved by hydrolysis, reduction reactions, oxidative reactions, pH shifts, photolysis, or combinations thereof; or by an enzyme reaction. Some linkers can be cleaved by an intracellular or extracellular enzyme, or an enzyme resulting from a microbial infection, a skin surface enzyme, or an enzyme secreted by a cell, by an enzyme secreted by a cancer cell, by an enzyme located on the surface of a cancer cell, by an enzyme secreted by a cell associated with a chronic inflammatory disease, by an enzyme secreted by a cell associated with rheumatoid arthritis, by an enzyme secreted by a cell associated with osteoarthritis, or by a membrane-bound enzyme. In some cases, the linker can be cleaved by an enzyme that is available in a target region. These types of linkers are often useful in that the particular enzyme or class of enzymes may be present in increased concentrations at a target region. The target tissue generally varies based on the type of disease or disorder present in the subject.

The linker may also comprise a bond that is cleavable under oxidative or reducing conditions, or may be sensitive to acids. Acid cleavable linkers can be found in U.S. Pat. Nos. 4,569,789 and 4,631,190; and Blattner, et al., *Biochemistry* (1984) 24:1517-1524. Such linkers are cleaved by natural acidic conditions, or alternatively, acid conditions can be induced at a target site as explained in U.S. Pat. No. 4,171,563.

A non-limiting set of molecules that can form acid cleavable bonds include cis-polycarboxylic alkenes (see U.S. Pat. No. 4,631,190), and amino-sulfhydryl cross-linking reagents which are cleavable under mildly acidic conditions (see U.S. Pat. No. 4,569,789). The linker may comprise a time-release bond, such as a biodegradable and/or hydrolyzable bond, such as esters, amides or urethane bonds.

Examples of linking reagents which contain cleavable disulfide bonds (reducible bonds) include 1,4-di-[3'-(2'-pyridyldithio)propionamido]butane; N-succinimidyl(4-azidophenyl)1,3'-dithiopropionate; sulfosuccinimidyl (4-azidophenyldithio)propionate; dithio bis(succinimidyl propionate); 3,3'-dithio bis(sulfosuccinimidylpropionate); dimethyl 3,3'-dithiobispropionimidate-2HCl (available from Pierce Chemicals, Rockford, Ill.).

Examples of oxidation sensitive linking reagents include, without limitation, disuccinimidyl tartarate; and disuccinimidyl tartarate (available from Pierce Chemicals).

The linker may also comprise a small molecule such as a peptide linker. Frequently, in such embodiments, the peptide linker is cleavable by base, under reducing conditions, or by a specific enzyme. The linker may be cleaved by an indigenous enzyme, or by an non-indigenous enzyme administered after or in addition to the presently contemplated compositions. A small peptide linker is pH sensitive, for example, the linker may comprise linkers selected from the group consisting of poly L-glycine; poly L-glutamine; and poly L-lysine linkers.

For example, the linker may comprise a hydrophobic polymer and a dipeptide, L-alanyl-L-valine (Ala-Val), cleavable by the enzyme thermolysin. This linker is advantageous because thermolysin-like enzyme has been reported to be expressed at the site of many tumors. A linker may also be used that contains a recognition site for the protease furin. Goyal, et al., *Biochem. J.* (2000) 2:247-254.

The chemical and peptide linkers can be bonded between the ligand and the agent by techniques known in the art for conjugate synthesis, i.e., using genetic engineering or chemically.

Photocleavable linkers include, for example, 1-2-(nitrophenyl)-ethyl. A photocleavable linker often permits the activation and action of the active agent in a very specific area, for example at a particular part of the target tissue. Activation (light) energy can be localized through a variety of means including catheterization, via natural or surgical openings or via blood vessels.

The linkers and techniques for providing coupling of the active to the hydrophobic moiety are similar to those that have been used previously to prepare conjugates to make actives more soluble, in contrast to their application in the present invention. In general, in the constructs of the invention, the active is often, but not always, made less soluble in aqueous solution by virtue of forming the conjugate. For example, the techniques reviewed by Greenwald, et al., for attaching PEG to small organic molecules can be adapted to the present invention. Some of these techniques are described in Greenwald, R. B., *Journal of Controlled*

*Release* (2001) 74:159-171; Greenwald, R. B., et al., *Journal of Medicinal Chemistry* (1996) 39:424-431; and Greenwald, R. B., et al., *Advanced Drug Delivery Reviews* (2002) 55:217-250. In particular, paclitaxel esters have been prepared via conjugation of PEG acids to the α-position on the paclitaxel molecule. These esters were demonstrated to be an especially effective linking group, as hydrolysis of the ester carbonyl bond and the subsequent release of the attached drug were shown to occur in a predictable fashion in vitro. (Greenwald, R. B., et al., *Critical Reviews in Therapeutic Drug Carrier Systems* (2000) 17:101-161.) The linker chemistry as applied in the present invention does not enhance solubility, but adapts the active for inclusion in the particulate vehicles of the invention.

The covalent attachment of proteins, vaccines or peptides to PEG can also be adapted to form the present conjugate. Such techniques are reviewed in Katre, N. V., *Advanced Drug Delivery Reviews* (1993) 10:91-114; Roberts, M. J., et al., *Journal of Pharmaceutical Sciences* (1998) 87:1440-1445; Garman, A. J., et al., *Febs Letters* (1987) 223:361-365; and Daly, S. M., et al., *Langmuir* (2005) 21:1328-1337. Coupling reactions between amino groups of proteins and mPEG equipped with an electrophilic functional group have been used in most cases for preparation of PEG-protein conjugates. The most commonly used mPEG-based electrophiles, referred to as 'activated PEGs' are based on reactive aryl chlorides, acylating agents and alkylating groups as described by Zalipsky, S., *Advanced Drug Delivery Reviews* (1995) 16:157-182; and Zalipsky, S., *Bioconjugate Chem.* (1995) 6:150-165. Tailoring the number of ethylene groups in the linker can additionally be used to adjust the hydrolysis rates of drug-linked ester bonds, to values appropriate for once-a-week administration. For example, Schoenmakers, et al., demonstrated the conjugation of a model paclitaxel molecule to PEG using a hydrolysable linker based on reaction between a thiol and an acrylamide. By changing the length of the linker, the time of drug release was varied between 4 and 14 days. (Schoenmakers, R. G., et al., *Journal of Controlled Release* (2004) 95:291-300.) Additionally, Frerot, et al., prepared a series of carbamoyl esters of maleate and succinate and studied the rate constants for neighboring group assisted alkaline ester hydrolysis. The rates of hydrolysis were found to depend on the structure of the neighboring nucleophile that attacks the ester function. (de Saint Laumer, J. Y., et al., *Helvetica Chimica Acta* (2003) 86:2871-2899.) By taking account of the influence of structural parameters on the rates of ester hydrolysis, hydrolysis rates may be varied over several orders of magnitude and precursors yielding the desired release profile may be designed.

In addition to ester linkages, enzymatically cleavable bonds can be used to conjugate active agents to the hydrophobic moiety. An enzymatically cleavable linker generally will comprise amino acids, sugars, nucleic acids, or other compounds which have one or more chemical bonds that can be broken via enzymatic degradation. In a recent study, a variety of amino acid spacers were employed for the conjugation of PEG to camptothecin, an anti-tumor drug. Rates of amino acid linker hydrolysis were determined to vary according to the type of amino acid spacer utilized. (Conover, C. D., et al., *Anti-Cancer Drug Design* (1999) 14:499-506.)

Photocleavable linkers have also been extensively employed for the synthesis of conjugates for release of actives. As an example, keto-esters have been used as delivery systems for the controlled release of perfumery aldehydes and ketones. Alkyl or aryl α-keto esters of primary or secondary alcohols decompose upon radiation at 350-370 nm, releasing the active aldehyde. (Rochat, S., et al., *Helvetica Chimica Acta* (2000) 83:1645-1671.) This mechanism has been shown to successfully sustain release of the active agent. For drug delivery purposes, light energy can be localized through a variety of means including catheterization, via natural and surgical openings or via blood vessels.

As noted above, when the linker is the residue of a divalent organic molecule, the cleavage "of the linker" may be either within the residue itself, or it may be at one of the bonds that couples the linker to the remainder of the conjugate—i.e., either to the active or the hydrophobic moiety.

In some embodiments, it is unnecessary for the linker to be cleavable. In particular, if the active is functional while still coupled to the linker, there is no need to release the active from the particulate moiety. One such example would be instances wherein the active is printer's ink, which can remain in particulate form when employed.

In instances where the linker need not be cleavable, alternative organic moieties may be used to create the divalent residue, or a covalent bond directly coupling the active to the hydrophobic moiety may not be subject to cleavage under conditions contemplated in use. (By "non-cleavable" is meant that the linker will not release the active under the conditions wherein the function of the active is being performed.) Examples of non-cleavable linkers comprise, but are not limited to, (sulfosuccinimidyl 6-[alpha-methyl-alpha-(2-pyridylthio)toluamido]hexanoate; Azidobenzoyl hydrazide; N-Hydroxysuccinimidyl-4-azidosalicyclic acid; Sulfosuccinimidyl 2-(p-azidosalicylamido)ethyl-1,3-dithiopropionate; N-{4-(p-azidosalicylamido)buthy}-3'(2'-pyidyldithio)propionamide; Bis-[beta-(4-azidosalicylamido)ethyl]disulfide; N-hydroxysuccinimidyl-4 azidobenzoate; p-Azidophenyl glyoxal monohydrate; N-Succiminidyl-6(4'-azido-2'-mitrophenylamino)hexanoate; Sulfosuccinimidyl 6-(4'-azido-2'-nitrophenylamino)hexanoate; N-5-Azido-2-nitrobenzyoyloxysuccinimide; Sulfosuccinimidyl-2-(m-azido-o-mitrobenzamido)-ethyl-1,3'-dithiopropionate; p-nitrophenyl-2-diazo-3,3,3-trifluoropropionate; Succinimidyl 4-(N-maleimidomethyl)cyclohexane-1-carboxylate; Sulfosuccinimidyl 4-(N-maleimidomethyl)cyclohexane-1-carboxylate; m-Maleimidobenzoyl-N-hydroxysuccinimide ester; m-Maleimidobenzoyl-N-hydroxysulfosuccinimide ester; N-Succinimidyl(4-iodoacetyl)aminobenzoate; N-Sulfosuccinimidyl(4-iodoacetyl)aminobenzoate; Succinimidyl 4-(p-malenimidophenyl)butyrate; Sulfosuccinimidyl 4-(p-malenimidophenyl)butyrate; Disuccinimidyl suberate; bis(sulfosuccinimidyl)suberate; Bis maleimidohexane; 1,5-difluoro-2,4-dinitrobenzene; dimethyl adipimidate 2HCl; Dimethyl pimelimidate-2HCl; dimethyl suberimidate-2-HCl; "SPDP"-N-succinimidyl-3-(2-pyridylthio)propionate; Sulfosuccinimidyl 4-(p-azidophenyl)butyrate; Sulfosuccinimidyl 4-(p-azidophenylbutyrate); 1-9p-azidosalicylamido)-4-(iodoacetamido)butane; 4-(p-Azidosalicylamido) butylamine (available from Pierce Chemicals).

Hydrophobic Moieties

A third component of the constructs of the invention is a hydrophobic moiety. The hydrophobic moiety may include polymers or natural products. Examples of suitable hydrophobic polymeric moieties include but are not limited to polymers of the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinylimidazole; aminoalkyls including aminoalkylacrylates, amino alkylmethacrylates, and aminoalkyl(meth)acrylamides; styrenes; cellulose acetate phthalate, cellulose acetate succinate, hydroxypropylmethylcellulose phthalate, and the polymers poly(D,L lactide), poly(D, L-lactide-co-glycolide), poly(glycolide), poly (hydroxybutyrate), poly(alkylcarbonate) and poly (orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) *Polymers in Controlled Drug Delivery*, Wright, Bristol, 1987; Arshady, *J. Controlled Release* (1991) 17:1-22; Pitt, *Int. J. Phar.* (1990) 59:173-196; Holland, et al., *J. Controlled Release* (1986) 4:155-180); hydrophobic peptide-based polymers and copolymers based on poly(L-amino acids) (Lavasanifar, A., et al., *Advanced Drug Delivery Reviews* (2002) 54:169-190), poly (ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl-methylether and other vinyl ethers, polyamides (nylon 6,6), polyurethane, poly(ester urethanes), poly(ether urethanes), poly (ester-urea). Particularly preferred polymeric hydrophobes include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) For non-biologically related applications particularly preferred polymeric carriers include polystyrene, polyacrylates, and butadienes. The polymers must contain one or more functionizable groups which may be incorporated into the polymer by derivitization or may be inherent in the polymer chemistry. Polymers as hydrophobic moieties should have molecular weights between 800 and 200,000. The preferred range is 1,000 to 10,000 for polymers with mono or divalent functional sites. For polymers with a multiplicity of functional sites for derivation the preferred molecular weight of the polymer per conjugated active is 1,000 to 10,000.

Natural products with functional groups or groups that can be converted to functional groups for conjugation include: hydrophobic vitamins (for example vitamin E, vitamins K and A), carotenoids and retinols (for example beta carotene, astaxanthin, trans and cis retinal, retinoic acid, folic acid, dihydrofolate, retinyl acetate, retinyl palmitate), cholecalciferol, calcitriol, hydroxycholecalciferol, ergocalciferol, *ƒ*-tocopherol, *ƒ*-tocopherol acetate, *ƒ*-tocopherol nicotinate, and estradiol. The preferred natural product is vitamin E which can be readily obtained as a vitamin E succinate, which facilitates functionalization to amines and hydroxyls on the active species.

Hydrophobic, non polymeric and moieties include hydrocarbon molecules with solubilities less than 0.1 mg/ml that contain a functional group for can be derivatized to incorporate a functional group for conjugation. Molecules in this class include hydrophobic dyes and plasticizers. Examples include, but are not limited to, coumarin, diaminonaphthalene and other naphthalene derivatives, anthracene and its derivatives, nile red. Further examples can be found in *Handbook of Dyes and pH Indicators*. Examples of hydrophobic plasticizes include dioctylphthalate, dibutylphthalate, and its derivatives.

Depending on the nature of the hydrophobic moiety, it may be able to accommodate more than one, including substantially more than one active through a multiplicity of linking sites. Polymeric moieties may have as many as 100 sites whereby actives could be linked. Simpler hydrophobic moieties, such as Vitamin E, may provide only one such site. Thus, the number of actives coupled to a single hydrophobic moiety may be only 1, or may be 2, 5, 10, 25, 100 and more, and all integers in between. For instance, the polymers set forth above can readily be provided with a multiplicity of functional groups for coupling to the active. Difunctional hydrophobic moieties would include the hydrophobic polymer chains listed above that have two terminal OH, COOH, or $NH_2$ groups. Multifunctional hydrophobic moieties include all of those listed above that have multiple OH, COOH, or $NH_2$ groups on some or all of the monomer units on the polymer backbone. These functional groups are merely illustrative; other moieties which could form functional groups for linking include phenyl substituents, halo groups, and the like. Typically, when the hydrophobic moiety is a hydrophobic polymer, it may have multiple sites for linkage. When the hydrophobic moiety is a relatively small molecule, it will accommodate only the number of linkers for which it has available functional groups.

Amphiphilic Stabilizers

The fourth component is an amphiphilic stabilizer. Typically, the stabilizer is a copolymer of a hydrophilic block coupled with a hydrophobic block. Nanoparticles formed by the process of this invention can be formed with graft, block or random amphiphilic copolymers. These copolymers can have a molecular weight between 1,000 g/mole and 50,000 g/mole or more, or between about 3,000 g/mole to about 25,000 g/mole, or at least 2,000 g/mole. Alternatively, the amphiphilic copolymers used in this invention exhibit a water surface tension of at least 50 dynes/$cm^2$ at a concentration of 0.1 wt %.

Examples of suitable hydrophobic blocks in an amphiphilic copolymer include but are not limited to the following: acrylates including methyl acrylate, ethyl acrylate, propyl acrylate, n-butyl acrylate (BA), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinylimidazole; aminoalkyls including aminoalkylacrylates, aminoalkylmethacrylates, and aminoalkyl(meth)acrylamides; styrenes; cellulose acetate phthalate, cellulose acetate succinate, hydroxypropylmethylcellulose phthalate, poly (D,L lactide), poly(D,L-lactide-co-glycolide), poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids) and their copolymers (see generally, Illum, L., Davids, S. S. (eds.) *Polymers in Controlled Drug Delivery*, Wright, Bristol, 1987; Arshady, *J. Controlled Release* (1991) 17:1-22; Pitt, *Int. J. Phar.* (1990) 59:173-196; Holland, et al., *J. Controlled Release* (1986) 4:155-180); hydrophobic peptide-based polymers and copolymers based on poly(L-amino acids) (Lavasanifar, A., et al., *Advanced Drug Delivery Reviews* (2002) 54:169-190), poly (ethylene-vinyl acetate) ("EVA") copolymers, silicone rubber, polyethylene, polypropylene, polydienes (polybutadiene, polyisoprene and hydrogenated forms of these polymers), maleic anhydride copolymers of vinyl methylether and other vinyl ethers, polyamides (nylon 6,6), polyurethane, poly(ester urethanes), poly(ether urethanes), poly (ester-urea). Particularly preferred polymeric blocks include poly(ethylenevinyl acetate), poly(D,L-lactic acid) oligomers and polymers, poly(L-lactic acid) oligomers and polymers, poly(glycolic acid), copolymers of lactic acid and glycolic acid, poly(caprolactone), poly(valerolactone), polyanhydrides, copolymers of poly(caprolactone) or poly(lactic acid) For non-biologically related applications particularly preferred polymeric blocks include polystyrene, polyacrylates, and butadienes.

Examples of suitable hydrophilic blocks in an amphiphilic copolymer include but are not limited to the following: carboxylic acids including acrylic acid, methacrylic acid, itaconic acid, and maleic acid; polyoxyethylenes or poly ethylene oxide; polyacrylamides and copolymers thereof with dimethylaminoethylmethacrylate, diallyldimethylammonium chloride, vinylbenzylthrimethylammonium chloride, acrylic acid, methacrylic acid, 2-acrylamido-2-methylpropane sulfonic acid and styrene sulfonate, polyvinyl pyrrolidone, starches and starch derivatives, dextran and dextran derivatives; polypeptides, such as polylysines, polyarginines, polyglutamic acids; poly hyaluronic acids, alginic acids, polylactides, polyethyleneimines, polyionenes, polyacrylic acids, and polyiminocarboxylates, gelatin, and unsaturated ethylenic mono or dicarboxylic acids.

Preferably the blocks are either diblock or triblock repeats. Preferably, block copolymers for this invention include blocks of polystyrene, polyethylene, polybutyl acrylate, polybutyl methacrylate, polylactic acid, polycaprolactone, polyacrylic acid, polyoxyethylene and polyacrylamide. A listing of suitable hydrophilic polymers can be found in *Handbook of Water-Soluble Gums and Resins*, R. Davidson, McGraw-Hill (1980).

In graft copolymers, the length of a grafted moiety can vary. Preferably, the grafted segments are alkyl chains of 12 to 32 carbons or equivalent to 6 to 16 ethylene units in length. In addition, the grafting of the polymer backbone can be useful to enhance solvation or nanoparticle stabilization properties. A grafted butyl group on the hydrophobic backbone of a diblock copolymer of a polyethylene and polyethylene glycol should increases the solubility of the polyethylene block. Suitable chemical moieties grafted to the block unit of the copolymer comprise alkyl chains containing species such as amides, imides, phenyl, carboxy, aldehyde or alcohol groups. One example of a commercially available stabilizer is the Hypermer family marketed by Uniqema Co. The amphiphilic stabilizer could also be of the gelatin family such as the gelatins derived from animal or fish collagen.

Formation of the Particulate Constructs

A number of methods can be used to form the particulate constructs of the invention. One particularly useful method is a process termed "Nano Precipitation" as described by Johnson, B. K., et al., *AIChE Journal* (2003) 49:2264-2282 and U.S. 2004/0091546 incorporated herein by reference. This process is capable of producing controlled size, polymer-stabilized and protected nanoparticles of hydrophobic organics at high loadings and yields. The Nano Precipitation technique is based on amphiphilic diblock copolymer arrested nucleation and growth of hydrophobic organics. Amphiphilic diblock copolymers dissolved in a good solvent can form micelles when the solvent quality for one block is decreased. In order to achieve such a solvent quality change, a tangential flow mixing cell (vortex mixer) is used. The vortex mixer consists of a confined volume chamber where one jet stream containing the diblock copolymer and active agent dissolved in a water-miscible solvent is mixed at high velocity with another jet stream containing water, an anti-solvent for the active agent and the hydrophobic block of the copolymer. The fast mixing and high energy dissipation involved in this process provide timescales that are shorter than the timescale for nucleation and growth of particles, which leads to the formation of nanoparticles with active agent loading contents and size distributions not provided by other technologies. When forming the nanoparticles via Nano Precipitation, mixing occurs fast enough to allow high supersaturation levels of all components to be reached prior to the onset of aggregation. Therefore, the active agent(s) and polymers precipitate simultaneously, and overcome the limitations of low active agent incorporations and aggregation found with the widely used techniques based on slow solvent exchange (e.g., dialysis). The Nano Precipitation process is insensitive to the chemical specificity of the components, making it a universal nanoparticle formation technique.

In an exemplary procedure, the active agent conjugated polymer and stabilizing diblock copolymer of methoxy poly(ethylene glycol)-b-poly(ε-caprolactone) (mPEG-PCL, 5,000-2,900 g/mole, respectively), is dissolved in THF at a weight ratio of 1:1:1 to make a 0.3 wt % solution for each component. The resulting solution is loaded into a 100 ml gas tight syringe, which is fixed on a digitally controlled syringe pump. A 300 mM sucrose solution is prepared, loaded into a 100 ml gas tight syringe, and fixed on a second syringe pump. The syringes are connected to the vortex mixer inlet, and pumped through at flow rates of 12 and 120 ml/min for the active agent and the sucrose solution, respectively. At the mixer outlet, two samples are collected. The first sample is collected in a scintillation vial and analyzed for particle size by dynamic light scattering (DLS), and the second sample is collected in low temperature freezer vials, and freeze-dried. The freeze-drying cycle is the following: −40° C. overnight, −10° C. for a day, 4° C. for a day, and then room temperature for one day. DLS measurements are repeated at 1, 2, 8, 16 hours, and daily intervals for each sample to check for stability. The samples are checked visually for crystals/aggregates formation. The freeze-dried material are checked for the presence of any residual solvent (THF). A freeze-dried sample is dissolved in methanol to dissociate the nanoparticles, and the solution is tested for the presence of THF using CGC.

Other processes that may be used to form the particulate constructs of the invention include milling, emulsification-diffusion and emulsification-evaporation. These are well-known processes readily practiced by those of skill in the art. Milling involves precipitating the conjugated active species into a particulate form with a macroscopically large particle size. The precipitate is then pulverized by mechanical means in the presence of a grinding media and a stabilizing polymer or surface active agent. The process is described in U.S. Pat. Nos. 4,726,955; 5,518,738 and 5,145,684).

In these processes, it may be useful to include, in addition to the conjugate and the amphiphilic stabilizer, an excess of a reactive form of the hydrophobic moiety coupled with linker so that any excess free active can be captured, and additional stability can be imparted to the resulting particles.

One conventional emulsification method of microencapsulating an agent to form a microencapsulated product is disclosed in U.S. Pat. No. 5,407,609. This method involves dissolving or otherwise dispersing agents, liquids or solids, in a solvent containing dissolved wall-forming materials, dispersing the agent/polymer-solvent mixture into a processing medium to form an emulsion and transferring all of the emulsion immediately to a large volume of processing medium or other suitable extraction medium, to immediately extract the solvent from the microdroplets in the emulsion to form a microencapsulated product, such as microcapsules or microspheres. The most common method used for preparing polymer delivery vehicle formulations is the solvent emulsification-evaporation method. This method involves dissolving the polymer and drug in an organic solvent that is completely immiscible with water (for example, dichloromethane). The organic mixture is added to water containing a stabilizer, most often poly(vinyl alcohol) (PVA) and then typically sonicated.

As indicated above, the particulate construct that results may contain one or more than one of the conjugates described. Typically, a nanoparticulate size construct will comprise $10^3$-$10^4$ conjugates; larger microparticles might comprise $10^5$-$10^7$ conjugates.

The resulting particles may have a variety of sizes depending on the nature of the components and on the method used to form them. Typically, the particles range in size from 50 nm to as much as 5 µm. For in vivo applications, nanometer size particles, typically of the order of 200 nm or less are preferred. For other applications, larger particles may be desirable. Thus, the dimensions of the particles may range from as little as 50 nm to 100 nm, 200 nm, 500 nm, 1 µm or 5 µm and the integers between. A composition of these constructs may contain a variety of sizes and can be described in terms of an average or median diameter.

After the particulate constructs are formed, they may be assessed for active agent loading content, size, and in vitro active agent release. Methods are available to assess the degree of polymer-active interaction or compatibility, including DSC, powder X-ray diffraction, and FTIR.

As one example of a procedure to measure the content of active agent, paclitaxel encapsulated in nanoparticles is assessed as follows. A sample of the freeze-dried material is weighed and dissolved in THF to solubilize the particles, then the sample is placed in a semi-micro spectrophotometer cell, and the paclitaxel concentration is determined using a UV spectrophotometer at 261 nm In addition, the absorbance is measured at 350 nm, and polymer only solutions is run at 261 nm as controls. The results obtained by UV analysis are confirmed using high performance liquid chromatography (HPLC) with a C18 column, methanol and water as mobile phases ranging from 10 to 100% methanol by volume, at a flow rate of 1 ml/min and 261 nm detection wavelength. The amount of cisplatin encapsulated in the nanoparticles is determined using atomic absorption spectrometry.

Particle size may be determined by DLS. For example, in one illustration, measurements are performed using an Nd-YAG laser with a 532 nm wavelength at a scattering angle of 90°. The sample collected in a scintillation vial from the mixer effluent is inserted into the DLS sample cell containing decalin scintillation fluid (maintained at 25° C. using a temperature bath), and left to equilibrate to the cell temperature. The run duration is 60 seconds, replicated three times. The particle size expressed as the hydrodynamic diameter is obtained using an ALV 5000 correlator and a second order cumulant fit.

In vitro release can also be measured. For the paclitaxel containing particles described above, 10 mM phosphate, 150 mM NaCl buffer solution is prepared, and active agent nanoparticles are suspended in 2 ml of the buffer solution to form a 1 mg/ml to a 5 mg/ml solution. The solution is introduced into a 12-14K dialysis membrane bag, and placed in 1 liter of the buffer solution at room temperature. 0.05 ml aliquots are collected from the dialysis bag and 1 ml of THF is added to dissociate the nanoparticles. The resulting solution is placed in semi-micro spectrophotometer cells, and the paclitaxel concentration is determined using a UV spectrophotometer at 261 nm In addition, the absorbance is measured at 350 nm, and polymer only solutions is run at 261 nm as controls. The cisplatin amounts are determined using atomic absorption spectrometry. The measurements are repeated at intervals of 1, 2, 4, 8, 16, 24, 48, and 72 hours.

The physical state of the active agent can also be studied by DSC. DSC thermograms of pure active agent, empty polymer nanoparticles or films and active agent-loaded polymer nanoparticles or films are recorded. The concentration of active agent ranges from 10-75% (w/w). The values for the heat of melting ($\Delta H_m$, J/g of active agent) of the active agent at each active agent concentration are recorded and a plot of $\Delta H_m$ versus concentration is prepared. The solid-state solubility (saturation solubility) of the active agents in the nanoparticles or films is determined by the y-intercept of the plot (Puttipipatkhachorn, et al., *J. Controlled Release* (2001) 10:75(1-2):143-153). Below the solid-state solubility the active agent is in a dissolved state while above that it exists in both a dissolved state and a crystalline state.

The solid-state solubility of the active agent is dependent on the molecular weight of the polymer. The higher the molecular weight of the polymer, the greater the microviscosity of the medium and the more difficult it is for the active agent to crystallize. Therefore, an increase in polymer molecular weight should act to increase the saturation solubility of an active agent.

Active agent-polymer interaction or compatibility is frequently assessed by DSC. The active agent may act as a plasticizer causing a decrease in the $T_g$ of the polymer or as a reinforcing filler resulting in an increase in the $T_g$ of the polymer. The criterion for polymer-active agent miscibility often comprises the presence of a single concentration dependent $T_g$ lying between the $T_g$'s of the individual components.

The miscibility of the polymer blends is frequently assessed using DSC. The DSC thermograms of each polymer and the polymer blend are recorded. The glass transition temperatures ($T_g$) of each component alone is compared to the $T_g$ value(s) in the polymer blends. The criterion for polymer-polymer miscibility is the same as that set out above for polymer-active agent miscibility.

The state of the active agent in polymer films or nanoparticles may be determined from diffractograms obtained from Powder X-ray diffraction (PXRD) patterns of the pure active agent, physical mixtures and the active agent-polymer blends. The presence of sharp peaks in the diffractogram indicates that the active agent is present in a crystalline state; while, a halo pattern indicates an amorphous state.

Polymer-active agent interactions may be measured using FTIR spectroscopy. The transmission infrared spectra of pure active agent, physical mixtures of pure active agent and polymer as well as films of the active agent-polymer blends are obtained. Interactions in the blend will result in band shifts and broadening in the FTIR spectrum when compared to the spectra for the pure polymer and active agent.

Applications and Uses of the Invention Particulate Constructs

In instances where the active is a therapeutic agent or a diagnostic agent useful in vivo, the particulate constructs are formulated into suitable veterinary or pharmaceutical compositions and administered to subjects as appropriate. The subjects include warm-blooded animals, including humans, domestic avian species, fish and the like. For treatment of human ailments, a qualified physician will determine how the compositions of the present invention should be utilized with respect to dose, schedule and route of administration using established protocols. Such applications also frequently utilize dose escalation should agents encapsulated in delivery vehicle compositions of the present invention exhibit reduced toxicity to healthy tissues of the subject.

The pharmaceutical or veterinary compositions of the present invention may be administered parenterally, i.e., intraarterially, intravenously, intraperitoneally, subcutaneously, or intramuscularly, the pharmaceutical compositions are administered, e.g., by a bolus or infusional injection. For example, see Rahman, et al., U.S. Pat. No. 3,993,754; Sears, U.S. Pat. No. 4,145,410; Papahadjopoulos, et al., U.S. Pat. No. 4,235,871; Schneider, U.S. Pat. No. 4,224,179; Lenk, et al., U.S. Pat. No. 4,522,803; and Fountain, et al., U.S. Pat. No. 4,588,578.

In other methods, the formulations of the invention can be contacted with target tissue by direct application of the preparation to the tissue. The application may be made by "topical", "open" or "closed" procedures. By "topical," it is meant the direct application of the multi-active agent preparation to a tissue exposed to the environment, such as the skin, oropharynx, external auditory canal, and the like. "Open" procedures are those procedures that include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Alternatively, the preparations may be administered through endoscopic devices, pumping devices, stents, wafers, reservoirs, pastes or films.

Pharmaceutical or veterinary compositions comprising delivery vehicles of the invention are prepared according to standard techniques and may comprise water, buffered water, 0.9% saline, 0.3% glycine, 5% dextrose, iso-osmotic sucrose solutions and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like.

Depending on the nature of the active agent, the formulation similar to those above may also be applied for cosmetic purposes and the excipients modified accordingly.

Combination Therapies

A particularly significant application of the present techniques is its use to deliver combinations of therapeutic agents, including multidrug resistance modulators, and imaging agents. Where biologically active combinations are used, the pharmacokinetics of the delivery are controlled by the particulate constructs used to deliver them and the nature of the cleavable linkers employed. Coordination of delivery of such agents to target tissues or organs is assured by suitable control of these parameters. It is particularly advantageous to deliver such agents in a ratio that is non-antagonistic, and especially that is non-antagonistic over a wide range of concentrations. As described in PCT publication PCT/CA02/01500, algorithms are available such that based on the results of in vitro tests, such non-antagonistic ratios may be determined. As noted in this publication, coordinated delivery of the specified ratio may be effected by including more than a single active in a particulate construct, or separate particulate constructs may be used. In the present case, if separate constructs are employed, the pharmacokinetics and release mechanisms of each construct are engineered to provide the desired ratio maintenance.

These techniques are described in detail in the foregoing publication; however, briefly, a preferred method is the Chou-Talalay median-effect method which utilizes an equation wherein the dose that causes a particular effect, $f_a$, is given by:

$$D=D_m[f_a/(1-f_a)]^{1/m}$$

in which D is the dose of the active agent used, $f_a$ is the fraction of cells affected by that dose, $D_m$ is the dose for median effect signifying the potency and m is a coefficient representing the shape of the dose-effect curve (m is 1 for first order reactions).

This equation can be further manipulated to calculate a combination index (CI) on the basis of the multiple active agent effect equation as described by Chou and Talalay, *Adv. Enzyme Reg.* (1984) 22:27-55; and by Chou, et al., in: *Synergism and Antagonism in Chemotherapy* (1991) 223-244, Chou and Rideout, eds., Academic Press: New York. A computer program (CalcuSyn) for this calculation is found in Chou and Chou ("Dose-effect analysis with microcomputers: quantitation of ED50, LD50, synergism, antagonism, low-dose risk, receptor ligand binding and enzyme kinetics": *CalcuSyn* Manual and Software; Cambridge: Biosoft 1987).

A two-active agent combination may be further used as a single pharmaceutical unit to determine synergistic or additive interactions with a third agent. In addition, a three-agent combination may be used as a unit to determine non-antagonistic interactions with a fourth agent, and so on.

The underlying experimental data are generally determined in vitro using cells in culture or cell-free systems. Preferably, the combination index (CI) is plotted as a function of the fraction of cells affected ($f_a$) as shown in FIG. 1A which, as explained above, is a surrogate parameter for concentration range. Preferred combinations of agents are those that display synergy or additivity over a substantial range of $f_a$ values. Combinations of agents are selected that display synergy over at least 5% of the concentration range wherein greater than 1% of the cells are affected, i.e., an $f_a$ range greater than 0.01. Preferably, a larger portion of overall concentration exhibits a favorable CI; for example, 5% of an $f_a$ range of 0.2-1.0. More preferably 10% of this range exhibits a favorable CI. Even more preferably, 20% of the $f_a$ range, preferably over 50% and most preferably over at least 70% of the $f_a$ range of 0.2 to 1.0 are utilized in the compositions. Combinations that display synergy over a substantial range of $f_a$ values may be re-evaluated at a variety of agent ratios to define the optimal ratio to enhance the strength of the non-antagonistic interaction and increase the $f_a$ range over which synergy is observed.

While it would be desirable to have synergy over the entire range of concentrations over which cells are affected, it has been observed that in many instances, the results are considerably more reliable in an $f_a$ range of 0.2-0.8. Thus, although the synergy exhibited by combinations of the invention is set forth to exist within the broad range of 0.01 or greater, it is preferable that the synergy be established in the $f_a$ range of 0.2-0.8. Other more sensitive assays, however, can be used to evaluate synergy at $f_a$ values greater than 0.8 for example bioluminescence or clonogenicity assays.

The optimal combination ratio may be further used as a single pharmaceutical unit to determine synergistic or additive interactions with a third agent. In addition, a three-agent combination may be used as a unit to determine non-antagonistic interactions with a fourth agent, and so on.

As set forth above, the in vitro studies on cell cultures will be conducted with "relevant" cells. The choice of cells will depend on the intended therapeutic use of the agent. Only one relevant cell line or cell culture type need exhibit the required non-antagonistic effect in order to provide a basis for the compositions to come within the scope of the invention.

For example, in a frequent embodiment, the combination of agents is utilized in anti-neoplastic therapy. Often, the combination of agents is intended for leukemia or lymphoma therapy. Appropriate choices will then be made of the cells to be tested and the nature of the test. In particular, tumor cell lines are suitable subjects and measurement of cell death or cell stasis is an appropriate end point. As will further be discussed below, in the context of attempting to find suitable non-antagonistic combinations for other indications, other target cells and criteria other than cytotoxicity or cell stasis could be employed.

For determinations involving antitumor agents, cell lines may be obtained from standard cell line repositories (NCI or ATCC for example), from academic institutions or other organizations including commercial sources. Preferred cell lines would include one or more selected from cell lines identified by the Developmental Therapeutics Program of the NCI/NIH. The tumor cell line screen used by this program currently identifies 60 different tumor cell lines representing leukemia, melanoma, and cancers of the lung, colon, brain, ovary, breast, prostate and kidney. The required non-antagonistic effect over a desired concentration range need be shown only on a single cell type; however, it is preferred that at least two cell lines exhibit this effect, more preferably three cell lines, more preferably five cell lines, and more preferably 10 cell lines. The cell lines may be established tumor cell lines or primary cultures obtained from patient samples. The cell lines may be from any species but the preferred source will be mammalian and in particular human. The cell lines may be genetically altered by selection under various laboratory conditions, and/or by the addition or deletion of exogenous genetic material. Cell lines may be transfected by any gene-transfer technique, including but not limited to, viral or plasmid-based transfection methods. The modifications may include the transfer of cDNA encoding the expression of a specific protein or peptide, a regulatory element such as a promoter or enhancer sequence or antisense DNA or RNA. Genetically engineered tissue culture cell lines may include lines with and without tumor suppressor genes, that is, genes such as p53, pTEN and p16; and lines created through the use of dominant negative methods, gene insertion methods and other selection methods. Preferred tissue culture cell lines that may be used to quantify cell viability, e.g., to test antitumor agents, include, but are not limited to, P388, L1210, HL-60, MOLT-4, KBM-3, WeHi-3, H460, MCF-7, SF-268, HT29, HCT-116, LS180, B16-F10, A549, Capan-1, CAOV-3, IGROV1, PC-3, MX-1 and MDA-MB-231.

In one preferred embodiment, the given effect ($f_a$) refers to cell death or cell stasis after application of a cytotoxic agent to a cell culture. Cell death or viability may be measured using known techniques.

Because combination therapy is particularly useful in the case of treatment of tumors, certain active agents are favored for use in combination when the target disease or condition is cancer. A non-limiting set of examples comprise the following: "Signal transduction inhibitors" which interfere with or prevents signals that cause cancer cells to grow or divide; "Cytotoxic agents"; "Cell cycle inhibitors" or "cell cycle control inhibitors" which interfere with the progress of a cell through its normal cell cycle, the life span of a cell, from the mitosis that gives it origin to the events following mitosis that divides it into daughter cells; "Checkpoint inhibitors" which interfere with the normal function of cell cycle checkpoints, e.g., the S/G2 checkpoint, G2/M checkpoint and G1/S checkpoint; "Topoisomerase inhibitors", such as camptothecins, which interfere with topoisomerase I or II activity, enzymes necessary for DNA replication and transcription; "Receptor tyrosine kinase inhibitors" which interfere with the activity of growth factor receptors that possess tyrosine kinase activity; "Apoptosis inducing agents" which promote programmed cell death; "Antimetabolites," such as Gemcitabine or Hydroxyurea, which closely resemble an essential metabolite and therefore interfere with physiological reactions involving it; "Telomerase inhibitors" which interfere with the activity of a telomerase, an enzyme that extends telomere length and extends the lifetime of the cell and its replicative capacity; "Cyclin-dependent kinase inhibitors" which interfere with cyclin-dependent kinases that control the major steps between different phases of the cell cycle through phosphorylation of cell proteins such as histones, cytoskeletal proteins, transcription factors, tumor suppresser genes and the like; "DNA damaging agents"; "DNA repair inhibitors"; "Anti-angiogenic agents" which interfere with the generation of new blood vessels or growth of existing blood vessels that occurs during tumor growth; and "Mitochondrial poisons" which directly or indirectly disrupt mitochondrial respiratory chain function.

Especially preferred combinations for treatment of tumors are the clinically approved combinations set forth hereinabove. As these combinations have already been approved for use in humans, reformulation to assure appropriate delivery is especially important.

Preferred agents that may be used in combination include DNA damaging agents such as carboplatin, cisplatin, cyclophosphamide, doxorubicin, daunorubicin, epirubicin, mitomycin C, mitoxantrone; DNA repair inhibitors including 5-fluorouracil (5-FU) or FUDR, gemcitabine and methotrexate; topoisomerase I inhibitors such as camptothecin, irinotecan and topotecan; S/G2 or G2/M checkpoint inhibitors such as bleomycin, docetaxel, doxorubicin, etoposide, paclitaxel, vinblastine, vincristine, vindesine and vinorelbine; G1/early-S checkpoint inhibitors; G2/M checkpoint inhibitors; receptor tyrosine kinase inhibitors such as genistein, trastuzumab, ZD1839; cytotoxic agents; apoptosis-inducing agents and cell cycle control inhibitors.

The mechanism of action of one or more of the agents may not be known or may be incorrectly identified. All synergistic or additive combinations of agents are within the scope of the present invention. Preferably, for the treatment of a neoplasm, combinations that inhibit more than one mechanism that leads to uncontrolled cell proliferation are chosen for use in accordance with this invention. For example, the present invention includes selecting combinations that effect specific points within the cell cycle thereby resulting in non-antagonistic effects. For instance, active agents that cause DNA damage can be paired with those that inhibit DNA repair, such as anti-metabolites. The present invention also includes selecting combinations that block multiple pathways that would otherwise result in cell proliferation.

Particularly preferred combinations are DNA damaging agents in combination with DNA repair inhibitors, DNA damaging agents in combination with topoisomerase I or topoisomerase II inhibitors, topoisomerase I inhibitors in combination with S/G2 or G2/M checkpoint inhibitors, G1/S checkpoint inhibitors or CDK inhibitors in combination with G2/M checkpoint inhibitors, receptor tyrosine kinase inhibitors in combination with cytotoxic agents, apoptosis-inducing agents in combination with cytotoxic agents, apoptosis-inducing agents in combination with cell-cycle control inhibitors, G1/S or G2/M checkpoint inhibitors in combination with cytotoxic agents, topoisomerase I or II inhibitors in combination with DNA repair inhibitors, topoisomerase I or II inhibitors or telomerase inhibitors in combination with cell cycle control inhibitors, topoisomerase I inhibitors in combination with topoisomerase II inhibitors, and two cytotoxic agents in combination.

Specific agents that may be used in combination include cisplatin (or carboplatin) and 5-FU (or FUDR), cisplatin (or carboplatin) and irinotecan, irinotecan and 5-FU (or FUDR), vinorelbine and cisplatin (or carboplatin), methotrexate and 5-FU (or FUDR), idarubicin and araC, cisplatin (or carboplatin) and taxol, cisplatin (or carboplatin) and etoposide, cisplatin (or carboplatin) and topotecan, cisplatin (or carboplatin) and daunorubicin, cisplatin (or carboplatin) and doxorubicin, cisplatin (or carboplatin) and gemcitabine, oxaliplatin and 5-FU (or FUDR), gemcitabine and 5-FU (or FUDR), adriamycin and vinorelbine, taxol and doxorubicin, flavopuridol and doxorubicin, UCN01 and doxorubicin, bleomycin and trichlorperazine, vinorelbine and edelfosine, vinorelbine and sphingosine (and sphingosine analogues), vinorelbine and phosphatidylserine, vinorelbine and camptothecin, cisplatin (or carboplatin) and sphingosine (and sphingosine analogues), sphingosine (and sphingosine analogues) and daunorubicin and sphingosine (and sphingosine analogues) and doxorubicin.

Preferred combinations in general include those set forth hereinabove as already shown to be efficacious in the clinic as recognized by the FDA and those further suggested based on literature reports. While the candidate agents for use in the method of the invention are not limited to these specific combinations, those set forth hereinabove have been disclosed as suitable combination therapies, and are thus preferred for use in the methods and compositions of the present invention.

The therapeutic agents in the present compositions may be formulated separately in individual compositions wherein each therapeutic agent is stably associated with appropriate delivery vehicles. These compositions can be administered separately to subjects as long as the pharmacokinetics of the delivery vehicles are coordinated so that the ratio of therapeutic agents administered is maintained at the target for treatment. Thus, it is useful to construct kits which include, in separate containers, a first composition comprising delivery vehicles stably associated with at least a first therapeutic agent and, in a second container, a second composition comprising delivery vehicles stably associated with at least one second therapeutic agent. The containers can then be packaged into the kit.

The kit will also include instructions as to the mode of administration of the compositions to a subject, at least including a description of the ratio of amounts of each composition to be administered. Alternatively, or in addition, the kit is constructed so that the amounts of compositions in each container is pre-measured so that the contents of one container in combination with the contents of the other represent the correct ratio. Alternatively, or in addition, the containers may be marked with a measuring scale permitting dispensation of appropriate amounts according to the scales visible. The containers may themselves be useable in administration; for example, the kit might contain the appropriate amounts of each composition in separate syringes. Formulations which comprise the pre-formulated correct ratio of therapeutic agents may also be packaged in this way so that the formulation is administered directly from a syringe prepackaged in the kit.

Therapeutic activity of delivery vehicle compositions comprising two or more active agents may be measured after administration into an animal model. Preferably, the animal model comprises a tumor although delivery vehicle compositions may be administered to animal models of other diseases. Rodent species such as mice and rats of either inbred, outbred, or hybrid origin including immunocompetent and immunocompromised, as well as knockout, or transgenic models may be used.

Methods for evaluating efficacy in treatment of various conditions, including tumors, are well known in the art.

Non-Pharmaceutical Applications

Many ink jet printing inks are based on soluble dyes. These present two problems. First the soluble dyes are prone to "bleeding" and are not as water-fast as is desired, and second, the dye wicks into the paper prior to drying with a corresponding loss in color intensity. To overcome these problems one strategy is to use insoluble pigment particles. However, the range of colors obtained from soluble dyes is not matched by the pigments in particulate form. The current invention would allow the conjugation of dyes to hydrophobic linkers that would allow incorporation into nanoparticle form. The especially preferable embodiment of this technology would couple Flash Nano Precipitation to form narrow size distribution particles in the range of 200 nm with the conjugation scheme to incorporate otherwise soluble dyes. The Flash Nano-Precipitation process allows the incorporation of multiple colors into a single particle to effect color blending.

In many industrial and biological applications it is desirable to have fluorescently labeled particles in the size range 50 nm to 2,000 nm. These are most commonly made from polymeric emulsion polymerized lattices into which dyes are imbibed. Alternatively, fluorescent species are reacted onto the surface of the particles. See Polysciences, Inc., *Particle Catalog* for a listing of representative particles (website: polysciences.com). The imbibing route has limitations as to the dyes that are hydrophobic enough to be retained in the spheres, and the chemical reacting route has limitations as to the number of fluorescent molecules that can be attached to a single sphere. Furthermore, the production of these tracer particles requires independent steps of particle formation, and then post processing to introduce the fluorescent species. In the present invention it is possible to conjugate a wide range of fluorescent dyes to make them hydrophobic. Using the Flash Nano Precipitation process it is then possible to produce fluorescent particles with high levels of fluorescence, narrow particle size distribution, controlled particle size, and tailor surface functionality.

In many applications it is desirable to have fragrances that are released over time. For example in laundry fabric conditioners, spray deodorizers, and perfumes. With the present invention it is possible to conjugate fragrances and to keep them in a particulate, highly dispersed form. The fragrance can be released over time by the hydrolytic cleavage of the linking bond, or by light cleavage of a photocleavable bond.

Sunscreens for personal care operate by applying UV absorbing species to the skin. See for example *Chemical and Engineering News* (2005) 83:18-22. It has been found that particulate systems have the added advantage of absorbing and scattering UV light and, therefore, enhance the performance of these formulations. Several efficient UV absorbers are too readily soluble to remain on the skin after exposure to water. In the present invention, UV absorbers can be conjugated with hydrophobic moieties to enable incorporation into nanoparticles in long-lasting formulation. By incorporation of appropriate hydrophilic blocks on the particle surface, that include cationic and hydrogen bonding monomers, it would be possible to have the nanoparticle formulation adhere to the skin for prolonged periods of time.

The following examples are offered to illustrate but not to limit the invention.

Example 1

Conjugation of Paclitaxel to Vitamin E Succinate (VitES)

280 mg of VitES were dissolved in 20 ml of dichloromethane and brought to 0° C. Then, 27 μL of diisopropylcarbodiimide were added, followed by 150 mg of paclitaxel and 33 mg of dimethylaminopyridine. The reaction vessel was warmed to room temperature, and left to react for 16 hours. The reaction solution was washed with 0.1 N hydrochloric acid, dried with magnesium sulfate, filtered, and dried in vacuo. The product was characterized and verified to be paclitaxel-VitES by High Performance Liquid Chromatography (HPLC) and Nuclear Magnetic Resonance (NMR) analysis.

Example 2

Conjugation of Paclitaxel to Polycaprolactone with Terminal Carboxylic Acids

A. 79 mg of PCL (MW 2.2 kg/mole, PCL2.2) end-terminated with carboxylic acid groups were dissolved in 20 ml of dichloromethane and brought to 0° C. 26 μL of diisopropylcarbodiimide were added, followed by 146 mg of paclitaxel and 32 mg of dimethylaminopyridine. The reaction vessel was warmed to room temperature, left to react for 16 hours, and washed with 0.1 N hydrochloric acid, dried with magnesium sulfate, filtered, and dried in vacuo. The amount of excess paclitaxel in the reaction product was reduced by recrystallization from amyl acetate. The product was characterized and verified as PCL-paclitaxel by HPLC and NMR analysis.

B. The procedure of paragraph A was also carried out using PCL1.45 and PCL3.5.

Example 3

Nanoparticles with Methoxy Polyethylene Glycol-Polycaprolactone (mPEG-PCL) and Paclitaxel-VitE As a control, 15 mg of methoxy polyethylene glycol-(MW 5 kg/mole)-polycaprolactone (methoxy polyethylene glycol molecular weight of 5 kg/mole, PCL molecular weight of 7 kg/mole) (mPEG5-PCL7) in THF to make a 1 wt % solution (w:w) of mPEG5-PCL7. Then, 8 mg of paclitaxel and 10 mg of VitES were added to the solution and mixed using the vortex mixer at a flow rate of 12 ml/min against water at 120 ml/min. Crystals were visible about 20 minutes after mixing, and no particles were detected by Dynamic Light Scattering (DLS).

20 mg of mPEG5-PCL7 were dissolved in THF to make a 0.5 wt % solution. Then, 23 mg of paclitaxel-VitES along with 17.4 mg VitES prepared as described in Example 1 was added to make a 0.58 wt % paclitaxel-VitES solution, and mixed using the vortex mixer at a flow rate of 12 ml/min against water at 120 ml/min Nanoparticles with an average diameter of 126 nm, as determined by DLS, were formed. The nanoparticles size after 17 hours was 134 nm. No visible crystals or aggregates were observed in the sample.

Example 4

Nanoparticles of Methoxy Polyethylene Glycol-Polycaprolactone and Paclitaxel-PCL mPEG5-PCL6 was dissolved in THF to make a 0.5 wt % solution (w:w). Then, paclitaxel-PCL prepared as described in Example 2 was added to the solution to make a 0.5 wt % (w:w) of the conjugate. The resulting solution was mixed using the vortex mixer at a flow rate of 12 ml/min against water at 120 ml/min, yielding nanoparticles with an average diameter of 75 nm. The nanoparticles size after 60 hours was 93 nm.

Example 5

Rifampicin-VitES

Vitamin E succinate (1210 IU/g) (2273.0 mg, 4.28 mMol) was dissolved in 20 ml of anhydrous methylene chloride. To this solution at 0° C. were added DIPC (654.9 μl, 4.28 mMol), rifampicin (1762.1 mg, 2.14 mMol) dissolved in 20 ml of anhydrous methylene chloride, and DMAP (806.1 mg, 6.55 mMol). The resulting solution was warmed to room temperature and left for 16 hours. The reaction mixture was washed with 0.1 N HCl, dried, and evaporated in vacuo to yield the product as a red powder. $^{13}$C and $^{1}$H NMR and HPLC confined the function or Rifampicin-VitES.

Example 6

Comparative Example

Attempts were made to obtain nanoparticles by vortex mixing unconjugated rifampicin with block copolymer poly (ethylene glycol)-b-poly(caprolactone) (PEG-b-PCL) (5k-5k). Only when the initial concentration of rifampicin in solvent (dimethylformamide) is over 12 wt %, could rifampicin be precipitated. Below this concentration clear red solutions of the final product were produced. Dynamic light scattering showed no nanoparticles above the size of approximately 10 nm (the lower resolution limit of the autocorrelator).

of conjugated rifampicin in DMF is 4 wt %. And the particles were stable as shown by DLS. The results are shown in the table below.

Particle Formation with Rifampicin

| Sample # | Drug | polymer | solvent | Anti-solvent (3 streams) | Ratio | Drug solubility in mixed solution | Flow rate | description |
|---|---|---|---|---|---|---|---|---|
| 1 | Rifampicin conjugated with Vit E succinate 12 wt % | PEG-b-PCL (5k-5k) 2 wt % | DMF | pH 5.0 citrite buffer | 1:9 | — | DMF: 12 ml/min Buffer: 36 ml/min each | Lighter orange color compare with others. Most suspended in the solution. Some residue. |
| 2 | Rifampicin 12 wt % | No | DMF | pH 5.0 citrite buffer | 1:9 | 0.49 mg/ml | DMF: 12 ml/min Buffer: 36 ml/min each | Big junks quickly settle to the bottom. |
| 3 | Rifampicin 12 wt % | PEG-b-PCL (5k-5k) 2 wt % | DMF | pH 5.0 citrite buffer | 1:9 | 0.49 mg/ml | DMF: 12 ml/min Buffer: 36 ml/min each | Day 1-2, clear red. No particles observed by DLS. Particle size <10 nm; supersaturationS ≈4. But after 3 days will be the same as sample 4. |
| 4 | Rifampicin 12 wt % | PEG-b-PCL (5k-5k) 2 wt % | DMF | pH 5.5 citrite buffer | 1:9 | 0.52 mg/ml | DMF: 12 ml/min Buffer: 36 ml/min each | Sample crystallized on the glass walls after 3 days. |
| 5 | Rifampicin 12 wt % | PEO-b-PS (3k-1k) 2 wt % | DMF | pH 5.5 citrite buffer | 1:9 | 0.52 mg/ml | DMF: 12 ml/min Buffer: 36 ml/min each | Most solids suspended in the solution and stable. Some residues on the bottom. (similar to PEG-b-PCL at pH = 4.0) |
| 6 | Rifampicin conjugated with Vit E succinate 4 wt % | PEG-b-PCL (5k-5k) 2 wt % | DMF | pH 5.0 citrite buffer | 1:9 | — | DMF: 12 ml/min Buffer: 36 ml/min each | Lighter orange color compare with others. Stable solution. |
| 7 | Rifampicin 12 wt % | PEG-b-PCL (5k-5k) 2 wt % | DMF | pH 4.0 citrite buffer | 1:9 | — | DMF: 12 ml/min Buffer: 36 ml/min each | Similar to sample 5. |

For unconjugated rifampicin at concentrations above 12 wt % it was possible to make nanoparticles using a four stream vortex mixer. The conditions of the experiment are given below.
Drug: rifampicin
Polymer: PS-b-PEO (1k-3k)
Solvent: DMF
Stream 1: 341 mg rifampicin (12 wt %) and 56.9 mg PW-b-PEO (2 wt %) in 3 ml DMF.
Stream 2: pH 5.5 buffer solution.
Stream 3: pH 5.5 buffer solution.
Stream 4: pH 5.5 buffer solution.
Mixing conditions:
Stream 1: 12 ml/min
Stream 2, 3, 4: 36 ml/min
DLS results:
2 hours after the mixing:
average radius=170.69 nm
width=108.09 nm
Polydispersity index=0.402
The average radius was determined 4 hours after mixing to be 532.68 nm with a width of 335.68 nm and a polydispersity index of 0.397.

Example 7

Rifampicin-VitES Particles

Conjugated rifampicin from Example 5 was mixed with block copolymer poly(ethylene glycol)-b-poly(caprolactone) (PEG-b-PCL) (5k-5k) as described in Example 6. Stable particles were formed when the initial concentration Example 8

Conjugation of Rifampicin to Dicarboxyl PCL

Dicarboxyl PCL (5 kDa) (10700 mg, 2.14 mMol) was dissolved in 20 ml of anhydrous methylene chloride. To this solution at 0° C. were added DIPC (654.9 µl, 4.28 mMol), rifampicin (1762.1 mg, 2.14 mMol) dissolved in 20 ml of anhydrous methylene chloride, and DMAP (806.1 mg, 6.55 mMol). The resulting solution was taken out of the ice bath to warm to room temperature and left for 16 hours. The reaction mixture was washed with 0.1 N HCl, dried, and evaporated in vacuo to yield the product as a red powder. $^{13}C$ and $^{1}H$ NMR and HPLC confirmed the structure as rifampicin-PCL.

Example 9

Nanoparticles from Poly(Ethylene Glycol)-b-Poly(Caprolactone) and Rifampicin-PCL Conjugated rifampicin from Example 8 above was mixed with block copolymer poly(ethylene glycol)-b-poly(caprolactone) (PEG-b-PCL) (5k-5k) as described in Example 6. Stable nanoparticles were formed when the initial concentration of rifampicin-PCL in DMF is 4 wt %. And the particles were stable as shown by DLS.

Example 10

Estradiol-VitES Conjugation

α-Tocopherol succinate (530.8 g/mol) is dissolved in anhydrous dichloromethane at 0° C. 1,3-diisopropylcarbodiimide (DIPC, 152.9 g/mol), estradiol (272.39 g/mol) and 4-(dimethylamino)-pyridine (DMAP, 123.1 g/mol) are added to the solution at a molar ratio of 1.5:0.25:1.5 with respect to α-tocopherol succinate. The reaction mixture is warmed to room temperature and aged for a period of 70 hours to achieve near complete conversion to the conjugate. A 0.1 N HCl wash is employed following reaction completion for the removal of residual DMAP. The solution is evaporated to dryness and the solid product, estradiol-VitES, isolated. The product estradiol-VitES was characterized by High Performance Liquid Chromatography (HPLC) and Nuclear Magnetic Resonance (NMR) analysis.

Example 11

Estradiol-VitES Nanoparticle Formation

Control: Estradiol and methoxy-poly(ethylene glycol)-b-poly(ε-caprolactone) (mPEG-PCL, 5,000-2,900 g/mole, respectively), are dissolved in THF at a weight ratio of 1:1 to make a 0.3 wt % solution for each component. The resulting solution is loaded into a gas tight syringe, and impingement mixed with an anti-solvent (water) using the Confined Impinging Jet (CIJ) mixer at injection rates of 12 ml/min and 120 ml/min for THF and water, respectively. Estradiol loaded nanoparticles were unstable soon after particle formation (<30 minutes), as indicated by visual observation of aggregates. DLS analysis could not be performed due to the presence of these aggregates.

Standard mixing procedure was followed to produce estradiol-VitES loaded nanoparticles with the Confined Impinging Jet (CIJ) mixer. The estradiol-VitES along with the block copolymer were dissolved in THF at the aforementioned weight ratios and impingement mixed with DI water. The resulting nanoparticles demonstrated a less than 10% increase in radius over the course of 48 hours, as indicated by Dynamic Light Scattering (DLS) analysis. Additional stability was observed in particles where the reaction mixture comprises a 3:1 molar ratio of VitES to conjugated to estradiol-VitES with stability noted in excess of 30 days.

Example 12

Nanoparticles Containing Estradiol-VitES and Paclitaxel-VitES

An estradiol-VitES conjugate is prepared as in Example 10. A conjugate of paclitaxel-VitES is prepared as according to Example 1. Nanoparticles comprising both estradiol-VitES and paclitaxel-VitES were made by first dissolving 30 mg of methoxy polyethylene glycol-polycaprolactone (methoxy polyethylene glycol molecular weight of 5 kg/mole, PCL molecular weight of 7 kg/mole) (mPEG5-PCL7) in 3 ml of THF to make a 1 wt % solution (w:w) of mPEG5-PCL7. Then, 8.5 mg of paclitaxel-VitES and 6.5 mg of estradiol-VitES prepared as described in the previous examples were added to the mPEG5-PCL7 solution in THF with 15 mg VitES. The weight ratio of paclitaxel-VitES to estradiol-VitES is 1.27. The resulting solution was mixed using the vortex mixer at a flow rate of 12 ml/min against water at 120 ml/min, yielding nanoparticles with an average diameter of 107 nm as determined by DLS. No visible crystals or aggregates were observed in the sample.

Example 13

Nanoparticles Containing Neoplastic Agents

A hydrophobic polymer-paclitaxel conjugate is prepared in accordance with the methods set out in Greenwald, et al., supra (1996), which addressed the formation of water soluble Taxol-poly(ethylene glycol) prodrugs. Instead of using poly(ethylene glycol), we will use poly(caprolactone) with a carboxylic acid end group to form the active agent conjugate. The reaction scheme used by Greenwald is shown in FIG. 1.

Complex 2, as depicted in FIG. 1, provided a hydrolysis half-life of 2 h in human whole blood, as observed in Greenwald's work. The hydrolysis kinetics in Greenwald's work vary from $t_{1/2}$>72 hours in DI water at pH 5.7 to $t_{1/2}$>5.5 hours in PBS buffer at pH 7.4. In the present case, the prodrug is encapsulated in the hydrophobic core of the nanoparticle, and accordingly, different hydrolysis rates (e.g., slower) and half-lives (e.g., longer) are provided, since the water activity is lower in the hydrophobic core of the nanoparticle. Having paclitaxel bound to a homopolymer in the nanoparticle core acts as a crystallization site for free paclitaxel, resulting in increased active agent retention.

Figure 2:
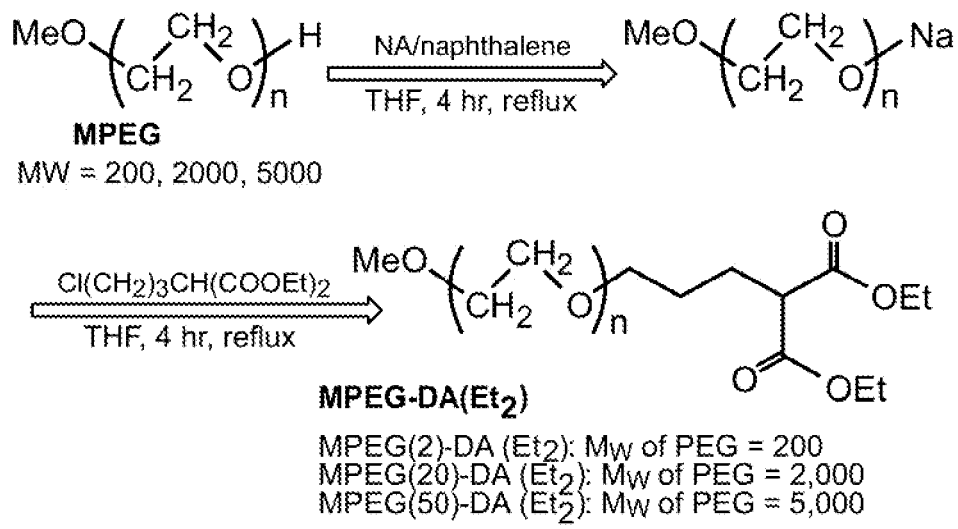
FIGS. 2A and 2B provide a depiction of poly(ethylene glycol) based cisplatin complex prepared by the method of Ohya, et al., *Polymers for Adv. Tech.* (2000) 11:635-641.
Figure 2:
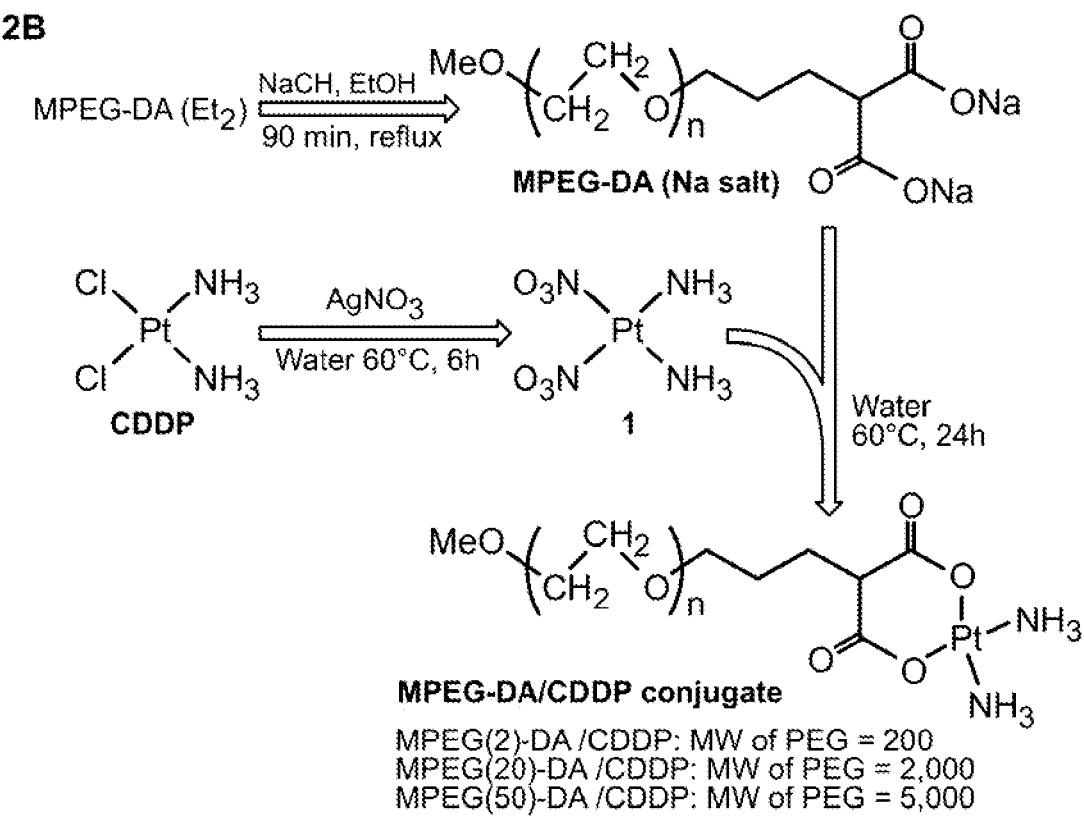

The same rationale is used to form cisplatin-polymer complexes. First, cisplatin is reacted with a mono acid or a diacid end group of a hydrophobic homopolymer to form a cisplatin-polymer complex, then the stabilizing diblock copolymer is added, and finally PEG-protected nanoparticles are formed using the vortex mixer. The cisplatin complex is prepared based on the work of Ohya, et al. supra (2000), where poly(ethylene glycol)-cisplatin complexes were prepared based on a 6-membered chelate-type dicarboxylate coordination bond, as shown in FIG. 2.

Example 14

Formulation of Synergistic Combinations in Polymer-Based Carriers; where One or More of the Agents has Both Unfavorable Water and Lipid Solubilities Four-two active agent combinations have been identified for purposes of this example. These include combinations comprising paclitaxel with cisplatin, etoposide with cisplatin, taxotere with doxorubicin, and paclitaxel with doxorubicin. These are formulated at particular ratios shown to be non-antagonistic.

Encapsulation Based on Hydrophobic Polymer-Active Agent Conjugation

It is hypothesized that the formation of a hydrophobic active agent-polymer conjugate using hydrophobic biodegradable polymers will provide an active agent release rate determined by the rate of chemical hydrolysis rather than diffusion. In addition, covalent attachment of the active agent to the hydrophobic block of the polymer will prevent Ostwald ripening of the nanoparticles and improve the stability of the formulation. Thus, although selected linkers are set forth below, a variety of other chemical linkers between the active agent and the polymer are contemplated as set forth herein. Coupling an active agent to a polymer using any of a variety of these linkers is accomplished in accordance with the presently described methods and others known and available in the art.

Paclitaxel-Hydrophobic Polymer Conjugate Formation

Novel Paclitaxel-polymer conjugates are prepared using hydrophobic polymers. The approach set out herein is based on the conjugation of paclitaxel to a homopolymer backbone before encapsulation using the diblock copolymer. First, paclitaxel is reacted with a hydrophobic homopolymer to form a paclitaxel-polymer conjugate, then the stabilizing diblock copolymer is added, and finally PEG-protected nanoparticles is formed using the vortex mixer. PCL and poly(lactide) with a terminal carboxylic acid group (PLA-COOH) are specifically investigated, but other polymers that are suitable are poly(lactide-co-glycolide)-COOH; poly(lactide)-COOH; poly(ε-caprolactone)-COOH and poly(β-benzyl-aspartate)-COOH.

Paclitaxel-PLA conjugate is prepared following Greenwald's procedure for making mPEG-paclitaxel prodrug. PLA-COOH (16,000 g/mole) is dissolved in dichloromethane to make a 3 wt % solution. The resulting solution is brought to 0° C., and diisopropylcarbodiimide (DIPC) is added at a molar ratio of 1.36:1 DIPC:PLA-COOH. Paclitaxel is then added at a molar ratio of 1:1 paclitaxel:DIPC. The reaction mixture is then warmed to room temperature, and left to react for 16 hours. A 0.1 N HCl is used for washing, and the solution is dried and evaporated in vacuo. The resulting solid is crystallized from 2-propanol and the product is analyzed using NMR. Nanoparticles of the active agent conjugate are then formed following the method outlined in the Formulation and Characterization section, using the active agent conjugate instead of the pure active agent. The experiment is repeated for paclitaxel-polymer: block copolymer weight ratios of 1:1, 1:3, and 1:10. The resulting nanoparticles are analyzed for size, active agent content, and in vitro release rates as outlined in the Formulation and Characterization section.

Cisplatin-Hydrophobic Polymer Complex Formation

Kataoka has demonstrated the formation of cisplatin complexes in water with homopolymers of poly(α,β-aspartic acid) and poly(ethylene glycol)-poly(glutamic acid) block copolymers, resulting in nanoparticles with cisplatin release times of approximately 14 hours. See Nishiyama, N., et al., *J. of Controlled Release* (2001) 74:83-94; see also Nishiyama, N., et al., *Cancer Research* (2003) 63:8977-8983.

In another embodiment, cisplatin-polymer conjugates are formulated using hydrophobic polymers. In this embodiment cisplatin is conjugated to a homopolymer end group prior to encapsulation using the diblock copolymer. PCL and poly(lactide) homopolymers having terminal diacid groups are described below. The present method is based on Ohya, Y., et al., (2000) (cited supra), to form poly(ethylene glycol)-cisplatin complexes.

Diacid diethyl ester terminated poly(lactide) (PLA-Da(Et)$_2$): 0.5 mMole of poly(lactide) is dissolved in 10 ml of anhydrous THF, and mixed with sodium and naphthalene (1.5 mMole). After refluxing under Ar atmosphere for 4 hours, diethylchloropropylmalonate (3 mMole) in 10 ml of THF is added to the reaction mixture, and refluxed for 4 hours under Ar. The final product is obtained by concentration and re-precipitation using diethyl ether. $^1$H-NMR is used to confirm the structure.

Cisplatin attachment to PLA-Da(Et$_2$): PLA-Da(Et$_2$) obtained from the above procedure is dissolved in 10 ml of ethanol (aq., 95%) and 243 mg of NaOH, and refluxed for 90 min. The resulting solution is subjected to an anion exchange resin column (QAE-Sephadex A-25, water then 2M-NaCl at 1 ml/min effluent) after refluxing for 90 minutes and re-precipitation using diethyl ether. The solution is then freeze-dried as described in the Formulation and Characterization section (above) to yield PLA-Da (Na salt). $^1$H-NMR is used to confirm the reaction. Cisplatin (50 mg) is dissolved in water and stirred for 3 h at 60° C., after which 0.22 ml of a 0.1 M silver nitrate solution is added and mixed at 60° C. for 6 h. The solution is filtered to remove precipitated silver chloride, and the filtrate dried in vacuo. The product is dissolved in THF and PLA-Da (Na salt) is added and left to react at 60° C. for 24 h. Gel-filtration chromatography is used to purify the sample, and the higher molecular weight fraction is freeze-dried as described in the Formulation and Characterization section. Atomic absorption spectrometry is used to determine the amounts of platinum in the complex.

Co-Formulation of Paclitaxel and Cisplatin

Subsequent to the successful encapsulation of each paclitaxel (or paclitaxel-polymer conjugate) and cisplatin-polymer complex, both agents are encapsulated in one carrier.

The nanoparticles encapsulating both paclitaxel (or corresponding polymer conjugate) and the cisplatin complex are formed by the following procedure. Each component (in active agent or complex form) is dissolved in THF to make a 0.3 wt % solution for each active agent. mPEG-PCL is added at a weight ratio of 1:1 mPEG-PCL:active agents. The nanoparticles then form, as outlined in the Formulation and Characterization section, using the cisplatin-polymer complex and the paclitaxel (or paclitaxel-polymer conjugate) instead of one active agent. The experiment is repeated for cisplatin:paclitaxel molar ratios of 1:5 and 5:1, and for active agents:block copolymer weight ratios of 1:1, 1:5 and 1:10. The resulting nanoparticles are analyzed for size, active agent content, and in vitro release rates as outlined in the Formulation and Characterization section.

Example 15

Controlled Delivery of Paclitaxel Using Stable Polymer-Based Formulations

This example demonstrates the stability and controlled release of paclitaxel from polymer-based nanoparticles formed via the presently described methods.

Material Storage and Stability

A paclitaxel formulation is prepared, lyophilized and redispersed in water to the primary particle size (determined before freeze-drying) using sucrose at a weight ratio of 60:1 sucrose:nanoparticles.

The stability of the paclitaxel nanoparticles in freeze-dried form is evaluated over a period of one month to demonstrate long term storage of the lyophilized material.

Lyophilized material obtained through the nanoparticle formation process as described in the Formulation and Characterization section is stored at 4° C. A sample is collected every week for the first month, then monthly and analyzed for size, active agent content, and in vitro release rate as outlined in the Formulation and Characterization section. The same procedure is repeated for a sample stored at room temperature.

In Vitro Active Agent Release Testing

The in vitro paclitaxel release rate from the nanoparticles is controlled to provide release half lives of >4 h.

Lyophilized nanoparticles containing paclitaxel are dissolved at a target active agent concentration of 1-5 mg/ml in water. The solution is diluted 2-10 fold in serum and incubated at 37° C. Aliquots are collected at 1, 2, 4, 8, 16, and 24 hours intervals, and assayed for paclitaxel. A Biogel A-0.5M gel filtration column is used to separate proteins and free active agent from the polymer-associated active agent. The paclitaxel concentration is determined as described in the Formulation and Characterization section.

In Vivo Active Agent Release Testing

In vivo paclitaxel release rate are evaluated through the injection of the active agent nanoparticles into mice IV at a paclitaxel dosage of 10 mg/kg. The target paclitaxel half life is 4 hours or longer. The plasma active agent elimination properties of polymer formulations are determined as a function of active agent/polymer ratio as well as hydrophobic/block co-polymer ratio.

Lyophilized nanoparticles containing paclitaxel are dissolved at a target active agent concentration of 1-5 mg/ml in water. The solution is diluted as necessary in saline to provide paclitaxel doses of 10 mg/kg in a volume of 0.2 ml. Following i.v. administration in mice at a dose of 20 mg/kg, plasma samples are collected at 1, 2, 4, 8, 16, and 24 hours intervals, and assayed for paclitaxel. The paclitaxel concentration is determined by HPLC analysis of a solvent-extracted sample.

Example 16

Matched PK for Polymer Formulation where the Synergistic Ratio of the Active Agent Combination is Maintained after I.V. Injection to Mice Nanoparticles containing both cisplatin and paclitaxel are investigated for in vivo release rates. The active agent ratios in the nanoparticles are dictated by the in vitro release rate results.

Lyophilized nanoparticles containing paclitaxel and cisplatin are dissolved at a target paclitaxel concentration of 1-5 mg/ml in water. The solution is diluted as necessary in saline to provide paclitaxel doses of 10 mg/kg in a volume of 0.2 ml. Following i.v. administration in mice, plasma samples are collected at 1, 2, 4, 8, 16, and 24 hours and assayed for paclitaxel. The paclitaxel and cisplatin concentrations are determined by HPLC and atomic absorption, respectively. The experiment is repeated at various paclitaxel:cisplatin ratios and for various polymer compositions until the synergistic ratio is maintained after i.v. injection.

Example 17

Evidence of Significant Antitumor Activity in Solid Tumor Model in Pilot Efficacy Studies In this embodiment, improved antitumor activity of a polymer conjugate COMBIPLEX™ formulation, described below, compared to free active agent cocktail in a human solid tumor xenograft model is evaluated.

A-COMBIPLEX™ formulation containing polymer conjugated paclitaxel and cisplatin at a molar ratio shown to be non-antagonistic in vitro and also exhibiting matched release rates for the two active agents is administered IV to mice bearing 100-200 mg solid tumors. The tumor selected is based on in vitro screening data where significant non-antagonism and preferably ratio dependency is observed. Dose range finding studies (3 mice per group) are first performed to establish MTD's in non-tumor bearing mice). For efficacy studies, mice (6 per group) are administered by IV a minimum of two different dose levels of COMBIPLEX™ and free active agent cocktail at approximate MTD's and at a matched dose of active agents in the COMBIPLEX™ formulation. Two treatment schedules are evaluated (weekly×3 and Q4D×3). Tumor weights are determined by measuring tumors using calipers. Animals are also monitored for signs of toxicity (weight loss and physical signs of stress).

Example 18

Additional Polymeric Nanoparticle Formulations

In accordance with the above methods, additional COMBIPLEX™ formulations are prepared utilizing a variety of combinations of anti-neoplastic agents. Agent combinations such as paclitaxel with etoposide, paclitaxel with taxotere, paclitaxel with doxorubicin, cisplatin with etoposide, cisplatin with taxotere, cisplatin with doxorubicin, etoposide with taxotere, etoposide with doxorubicin, doxorubicin with taxotere are prepared and evaluated. The chemical linkages are altered and adjusted to provide for desired release rates.

One of skill in the art would understand that alternative active agents can be substituted for those set forth in the above Examples. For example, other platinum analogs such as Carboplatin, Oxaliplatin, Tetraplatin, Platinum-DACH, Ormaplatin, among others, can be substituted for Cisplatin. Frequently, an active agent is substituted with another active agent within the same class, as discussed above. Often, however, any of a variety of the active agents set forth herein are combined in a nanoparticle formulation in accordance with the present materials and methods. Frequently, these nanoparticle formulations contain a combination of one or two or three or more active agents.

The invention claimed is:

1. A composition comprising particles obtained from fast mixing according to the Nano Precipitation process
   a) an amphiphilic stabilizer,
   b) a conjugate of the formula $$(\text{active–linker})_n\text{–hydrophobic moiety} \quad (1)$$

wherein n is an integer of 1-100;
   "active" refers to a first therapeutic agent;
   "linker" is a divalent residue of an organic molecule which comprises a bond that is selectively cleavable by reduction or hydrolysis to control the rate of release of said active from the particles free of said hydrophobic moiety or portion thereof; and
   "hydrophobic moiety" refers to the residue of an organic molecule that is insoluble in aqueous solution; and
   c) a second therapeutic agent different from the first therapeutic agent to obtain said particles,
   and wherein the hydrophobic moiety is a polymer having a molecular weight between 800 and 200,000 g/mole or is a natural product, and the amphiphilic stabilizer is a copolymer having a hydrophilic region and a hydrophobic region wherein said copolymer is a graft, block or random amphiphilic copolymer and has a molecular weight between 1,000 g/mole and 50,000 g/mole.

2. The composition of claim 1 wherein the hydrophobic moiety is a polymer of methyl acrylate, ethyl acrylate, propyl acrylate, n-butyl acrylate (BA), isobutyl acrylate, 2-ethyl acrylate, t-butyl acrylate, ethyl methacrylate, n-butyl methacrylate, isobutyl methacrylate, an acrylonitrile, a methacrylonitrile, vinyl acetate, vinylversatate, vinylpropionate, vinylformamide, vinylacetamide, vinylpyridine, vinylimidazole; an aminoalkylacrylate, an aminoalkylmethacrylate, an aminoalkyl(meth)acrylamide, a styrene, cellulose acetate phthalate, cellulose acetate succinate, hydroxypropylmethylcellulose phthalate, or
is poly(D,L lactide), poly(D,L-lactide-co-glycolide), poly(glycolide), poly(hydroxybutyrate), poly(alkylcarbonate), a poly(orthoester), a polyester, poly(hydroxyvaleric acid), polydioxanone, poly(ethylene terephthalate), poly(malic acid), poly(tartronic acid), a polyanhydride, a polyphosphazene, a poly(amino acid) and copolymers, a poly(ethylene-vinyl acetate) ("EVA") copolymer, silicone rubber, polyethylene, polypropylene, a polydiene, a maleic anhydride copolymer of vinylmethylether and other vinyl ethers, a polyamide (nylon 6,6), a polyurethane, a poly(ester urethane), a poly(ether urethane), a poly(ester-urea), poly(valerolactone), a polyanhydride, a copolymer of poly(caprolactone) and poly(lactic acid), or is a natural product which is vitamin E, vitamin K, vitamin A, beta carotene, astaxanthin, trans and cis retinal, retinoic acid, folic acid, dihydrofolate, retinyl acetate, retinyl palmitate), cholecalciferol, calcitriol, hydroxycholecalciferol, ergocalciferol, a-tocopherol, a-tocopherol acetate, a-tocopherol nicotinate, or estradiol.

3. The composition of claim 1 wherein the amphiphilic stabilizer is a copolymer of a hydrophilic block coupled with a hydrophobic block, wherein the hydrophobic block is methyl acrylate, ethyl acrylate, propyl acrylate, n-butyl acrylate (BA), isobutyl acrylate, 2-ethyl acrylate, t-butyl acrylate, ethyl methacrylate, n-butyl methacrylate, isobutyl methacrylate, an acrylonitrile; methacrylonitrile, vinyl acetate, vinylversatate, vinylpropionate, vinylformamide, vinylacetamide, vinylpyridine, vinylimidazole, an aminoalkylmethacrylate, an aminoalkyl(meth)acrylamide, styrene, cellulose acetate phthalate, cellulose acetate succinate, hydroxypropylmethylcellulose phthalate, poly(D,L lactide), poly (D,L-lactide-co-glycolide), poly(glycolide), poly(hydroxybutyrate), poly(alkylcarbonate), a poly(orthoester), a polyester, poly(hydroxyvaleric acid), polydioxanone, poly(ethylene terephthalate), poly(malic acid), poly(tartronic acid), a polyanhydride, a polyphosphazene, a poly(amino acid), a poly(ethylene-vinyl acetate) ("EVA") copolymer, silicone rubber, polyethylene, polypropylene, a polydiene, a hydrogenated form of polydiene), maleic anhydride copolymers of vinyl methylether and other vinyl ethers, polyamides (nylon 6,6), polyurethane, poly(ester urethanes), poly(ether urethanes), poly(ester-urea), poly(ethylenevinyl acetate), poly(D,L-lactic acid), poly(L-lactic acid), poly(glycolic acid), a copolymer of lactic acid and glycolic acid, poly(caprolactone), poly(valerolactone), a polyanhydride, a copolymer of poly(caprolactone) and poly(lactic acid); and the hydrophilic block is a carboxylic acid, a polyoxyethylene, a polyacrylamide, a copolymer of acrylamide with dimethylaminoethylmethacrylate, diallyldimethylammonium chloride, vinylbenzylthrimethylammonium chloride, acrylic acid, methacrylic acid, 2-acrylamido-2-methylpropane sulfonic acid, styrene sulfonate, polyvinyl pyrrolidone, starch, a starch derivative, dextran, a dextran derivative, a polypeptide, poly hyaluronic acid, an alginic acid, a polylactide, a polyethyleneimine, a polyionene, a polyacrylic acid, a polyiminocarboxylate, gelatin, or an unsaturated ethylenic mono or dicarboxylic acid.

4. The composition of claim 1, wherein the hydrophobic moiety is vitamin E, vitamin A or vitamin K, or a retinol; or wherein the hydrophobic moiety is polycaprolactone, polylactic acid, polystyrene, polybutadiene, polycaproic acid, polymethylbenzylate, poly(D,L-lactide), poly(D,L-lactide-co-glycolide), poly(glycolide), poly(hydroxybutyrate), poly(alkylcarbonate) poly(orthoesters), polyesters, poly(hydroxyvaleric acid), or copolymers thereof.

5. The composition of claim 1, wherein the amphiphilic stabilizer is methoxypolyethylene glycol (mPEG)-polycaprolactone (PCL), mPEG-polystyrene, mPEG-polybutadiene, mPEG-polylactate, block copolymers of polyethylene oxide, and polypropylene oxide, or block copolymers of polyethylene oxide and polybutylene oxide.

6. The composition of claim 1, wherein the particulate constructs comprise $10^3$-$10^7$ conjugates of formula (1).

7. The composition of claim 1, wherein the particulate constructs have an average diameter less than 5 μ.

8. The composition of claim 1 wherein said first therapeutic agent is present in the form of formula (1) and the second therapeutic agent is in unbound form.

* * * * *